United States Patent
Hafez et al.

(10) Patent No.: US 11,715,565 B2
(45) Date of Patent: Aug. 1, 2023

(54) EVALUATING EFFECT OF EVENT ON CONDITION USING PROPENSITY SCORING

(71) Applicant: Tempus Labs, Inc., Chicago, IL (US)

(72) Inventors: Ashraf Hafez, Chicago, IL (US); Caroline Epstein, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 658 days.

(21) Appl. No.: 16/679,054

(22) Filed: Nov. 8, 2019

(65) Prior Publication Data

US 2021/0142910 A1    May 13, 2021

(51) Int. Cl.
| | | |
|---|---|---|
| *G16H 50/30* | (2018.01) | |
| *G06F 3/01* | (2006.01) | |
| *G16H 50/70* | (2018.01) | |

(52) U.S. Cl.
CPC ............. *G16H 50/30* (2018.01); *G06F 3/011* (2013.01); *G16H 50/70* (2018.01)

(58) Field of Classification Search
CPC ......... G16H 50/30; G16H 50/70; G06F 3/011
See application file for complete search history.

(56) References Cited

U.S. PATENT DOCUMENTS

| | | | |
|---|---|---|---|
| 7,912,734 B2 | 3/2011 | Kil | |
| 2011/0257988 A1* | 10/2011 | Denekamp | G16H 50/30 706/54 |
| 2013/0144636 A1 | 6/2013 | Pouliot et al. | |
| 2013/0338453 A1* | 12/2013 | Duke | A61B 5/486 600/309 |
| 2014/0343959 A1* | 11/2014 | Hasegawa | G16H 70/60 705/2 |
| 2017/0103179 A1* | 4/2017 | Jiao | G16H 10/20 |
| 2017/0181711 A1* | 6/2017 | Cheng | A61B 5/0022 |
| 2018/0330824 A1* | 11/2018 | Athey | G16B 40/20 |

FOREIGN PATENT DOCUMENTS

WO    WO 2014/183023 A1    11/2014

OTHER PUBLICATIONS

Morid et al., Supervised Learning Methods for Predicting Healthcare Costs: Systematic Literature Review and Empirical Evaluation, AMIA ANNU SYMP PROC 1312-1321 (Apr. 16, 2018) (Year: 2018).*

(Continued)

*Primary Examiner* — Evangeline Barr
*Assistant Examiner* — Jordan L Jackson
(74) *Attorney, Agent, or Firm* — Morgan, Lewis & Bockius LLP

(57) ABSTRACT

Systems and methods are provided for implementing a tool for evaluating an effect on an event, such as a medication or treatment, on a subject's condition, using a propensity model that identifies matched treatment and control cohorts within a base population of subjects. A propensity value threshold, which can be obtained based on user input, can be used to adjust the selection of subjects for treatment and control cohorts. The tool allows analyzing features of the subjects in the treatment and control groups, and further allows for evaluation and comparison of survival objectives of subjects in the treatment and control groups.

45 Claims, 22 Drawing Sheets

(56) References Cited

OTHER PUBLICATIONS

Deb et al., A Review of Propensity-Score Methods and Their Use in Cardiovascular Research, 32(2) Canadian J of Cardiology 259-265 (Feb. 2016) (Year: 2016).*
Jackson et al., Propensity Scores in Pharmacoepidemiology: Beyond the Horizon, 4(4) Current Epidemiology Reports 271-280 (Dec. 1, 2018) (Year: 2018).*
Rosenbaum and Rubin, The central role of the propensity score in observational studies for causal effects, 70(1) BIOMETRIKA 41-55 (Year: 1983).*
Huber et al., Radius matching on the propensity score with bias adjustment: tuning parameters and finite sample behavior, 49 Empir Econ 1-31 (Year: 2015).*
Ray et al., Performance of Time-Dependent Propensity Scores: A Pharmacoepidemiology Case Study, 24(1) Pharmacoepidemiol Drug SAF. 98-106 (Jan. 2015) (Year: 2015).*
PCT Written Opinion of the International Searching Authority for WO2021091633A1 (dated Mar. 30, 2021) (Year: 2021).*
Mahalanobis distance | Wikipedia, the free encyclopedia, 2004. [Online; accessed Jul. 19, 2018], en.wikipedia.org/wiki/Mahalanobis_distance, pp. 1-5.
Austin, Peter C., "The use of propensity score methods with survival ortime-to-event outcomes: reporting measures of effect similar to those used in randomized experiments", Statistics in Medicine, 33, Sep. 3, 2013, pp. 1242-1258.
Austin, Peter C., et al. "Moving towards best practice when using inverse probability of treatment weighting (IPTW) using the propensity score to estimate causal treatment effects in observational studies", Statistics in Medicine, Aug. 3, 2015, 34(28), pp. 3661-3679.
Cole, Stephen R., et al. "Adjusted survival curves with inverse probability weights", Computer Methods and Programs in Biomedicine, Elsevier, 2004, 75, pp. 45-49.
Reinisch, June M., et al. "In Utero Exposure to Phenobarbital and Intelligence Deficits in Adult Men", Journal of the American Medical Association, Nov. 15, 1995, vol. 274, No. 19, pp. 1518-1525.
Rosenbaum, Paul R., et al. "The Central Role of the Propensity Score in Observational Studies for Causal Effects", Biometrika, vol. 70, No. 1, Apr. 1983, pp. 41-55.
Rosenbaum, Paul R., et al. "Constructing a Control Group Using Multivariate Matched Sampling Methods that Incorporate the Propensity Score", American Statistical Association, Feb. 1985, vol. 39, No. 1, pp. 33-38.
Stuart, Elizabeth A. "Matching methods for causal inference: a review and a look Forward", Statistical Science, 25(1), Feb. 1, 2010, pp. 1-29.
Hong, et al. "Feasibility Study Using Propensity Score Matching Methods for the Pseudo-Common Person Equating Requirement", OTJR: Occupation, Participation and Health, 2019, vol. 39(1), pp. 32-40.
Jackson, et al. "Propensity Scores in Pharmacoepidemiology: Beyond the Horizon", Curr Epidemiol Rep., Dec. 2017, 4(4), pp. 271-280.
Shi, et al. "Evaluation of the benefit of post-mastectomy radiotherapy in patients with early-stage breast cancer: A propensity score matching study", Oncology Letters, 17: 2019, pp. 4851-4858.

* cited by examiner

| Control | | Treatment | |
|---|---|---|---|
| Censorship rate | 0.54 | Censorship rate | 0.26 |
| Distinct meds (Pre) | 8.88 | Distinct meds (Pre) | 5.56 |
| Distinct meds (Post) | 7.43 | Distinct meds (Post) | 12.25 |

| Drugs Taken (Pre) | % | Drugs Taken (Pre) | % |
|---|---|---|---|
| dexamethasone | 2.9 | dexamethasone | 26.3 |
| docusate | 2.3 | docusate | 2 |
| heparin | 2.2 | heparin | 1.7 |
| ondansetron | 2.1 | ondansetron | 17.7 |
| acetaminophen / hydrocodone | 2 | acetaminophen / hydrocodone | 2.3 |
| cisplatin | 2 | cisplatin | 12.8 |
| sodium chloride | 1.7 | sodium chloride | 3.9 |
| morphine | 1.7 | morphine | 2.9 |
| palonosetron | 1.6 | palonosetron | 12.5 |
| magnesium sulfate | 1.4 | magnesium sulfate | 3.8 |

| Drugs Taken (Post) | % | Drugs Taken (Post) | % |
|---|---|---|---|
| dexamethasone | 19.8 | dexamethasone | 33.9 |
| ondansetron | 11.8 | ondansetron | 21.7 |
| cisplatin | 11.8 | cisplatin | 4 |
| palonosetron | 10.6 | palonosetron | 25.6 |
| lorazepam | 8.2 | lorazepam | 13.9 |
| etoposide | 8 | etoposide | 9.6 |
| fosaprepitant | 7.7 | fosaprepitant | 7.9 |
| prochlorperazine | 6.8 | prochlorperazine | 15.6 |
| pemetrexed | 5.8 | pemetrexed | 20.4 |
| magnesium sulfate | 5.1 | magnesium sulfate | 4.5 |

FIG. 5D

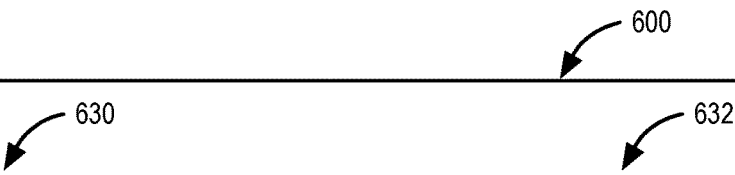

| Control | | Treatment | |
|---|---|---|---|
| Censorship rate | 0.64 | Censorship rate | .49 |
| Distinct meds (Pre) | 5.33 | Distinct meds (Pre) | 3.13 |
| Distinct meds (Post) | 4.91 | Distinct meds (Post) | 17.60 |
| Drugs Taken (Pre) | % | Drugs Taken (Pre) | % |
| capecitabine | 1.9 | capecitabine | 1.5 |
| ondansetron | 1.1 | ondansetron | 15.1 |
| sodium chloride | 1 | sodium chloride | 1.7 |
| acetaminophen | <1 | acetaminophen | 1.9 |
| acetaminophen / hydrocodone | <1 | acetaminophen / hydrocodone | <1 |
| lorazepam | <1 | lorazepam | 7 |
| meperidine | <1 | meperidine | <1 |
| magnesium chloride / potassium chloride / sodium acetate / sodium chloride / sodium gluconate | <1 | magnesium chloride / potassium chloride / sodium acetate / sodium chloride / sodium gluconate | <1 |
| prochlorperazine | <1 | prochlorperazine | 14 |
| ferumoxytol | <1 | ferumoxytol | <1 |
| Drugs Taken (Post) | % | Drugs Taken (Post) | % |
| capecitabine | 24.9 | capecitabine | 16.3 |
| ondansetron | 10.6 | ondansetron | 26.6 |
| dexamethasone | 9.8 | dexamethasone | 33.1 |
| prochlorperazine | 8.2 | prochlorperazine | 18.3 |
| oxaliplatin | 8 | oxaliplatin | 43.5 |
| palonosetron | 6.6 | palonosetron | 27.8 |
| lorazepam | 4.9 | lorazepam | 17.3 |
| sodium chloride | 4.6 | sodium chloride | 17.3 |
| bevacizumab | 4 | bevacizumab | 34.2 |
| ciprofloxacin | 3.7 | ciprofloxacin | 8.6 |

FIG. 6C

Impact of propensity score matching (range = low)

| Control | | Treatment | |
|---|---|---|---|
| Censorship rate | 0.4 | Censorship rate | 0.15 |
| District meds (Pro) | 2.6 | District meds (Pro) | 6.1 |
| District meds (Post) | 4.29 | District meds (Post) | 20.6 |
| Drugs Taken (Pre) | % | Drugs Taken (Pre) | % |
| oxaliplatin | 2.4 | oxaliplatin | 12.7 |
| capecitabine | 2.4 | capecitabine | 18.3 |
| exemestane | 1.2 | dexamethasone | 12.7 |
| dexamethasone | 1.2 | palonosetron | 10.3 |
| cyclophosphamide | 1.2 | pegfilgrastim | 1 |
| palonosetron | 1.2 | | |
| docetaxel | 1.2 | | |
| pegfilgrastim | 1.2 | | |
| miconazole | 1.2 | | |
| betamethasone / calcipotriene | 1.2 | | |

FIG. 9B

Impact of propensity score matching (range = mid)

| Control | | Treatment | |
|---|---|---|---|
| Censorship rate | 0.35 | Censorship rate | 0.2 |
| District meds (Pro) | 1.5 | District meds (Pro) | 3.94 |
| District meds (Post) | 5.28 | District meds (Post) | 22.35 |
| Drugs Taken (Pre) | % | Drugs Taken (Pre) | % |
| capecitabine | 2.1 | capecitabine | 2.5 |
| erythromycin | <1 | erythromycin | <1 |
| polyethylene glycol 3350 / potassium chloride / sodium bicarbonate / sodium chloride / sodium sulfate | <1 | polyethylene glycol 3350 / potassium chloride / sodium bicarbonate / sodium chloride / sodium sulfate | <1 |
| bacitracin / hydrocortisone / neomycin / polymyxin b | <1 | bacitracin / hydrocortisone / neomycin / polymyxin b | <1 |
| potassium chloride | <1 | potassium chloride | 1.8 |
| lidocaine / prilocaine | <1 | lidocaine / prilocaine | 5.3 |

FIG. 10B

EVALUATING EFFECT OF EVENT ON CONDITION USING PROPENSITY SCORING

TECHNICAL FIELD

The present disclosure relates generally to computer-implemented tools that use propensity scoring models to identify comparable test and control groups among a base subject population and that allow for evaluating an effectiveness of a treatment.

BACKGROUND

In pharmaceutical and medical fields, the common goal is to evaluate the effect of a drug or a therapy on patient's characteristics including those related to patient's survival. Proper evaluation of treatment effectiveness would allow prescribing treatments with precision, thereby avoiding or decreasing medical mistakes and increasing patient survival. This is a challenging task, given a multitude of patient's characteristics and differences between patients.

Selection and evaluation of a treatment or medication typically includes comparing patient populations. The standard way of performing clinical trials is randomized clinical trials. Observational, nonrandomized data analysis is another frequently used approach. The observational data analysis differs from randomized trials in that there is no reason to believe that populations being studied are free of correlation with an observed outcome. For example, comparison of breast cancer patients who had surgery to those breast cancer patients who did not have a surgery can be akin to comparing apples and oranges, because the patients that had surgery had a reason for their surgery (meaning that they were not selected at random) and they are thus fundamentally different from those patients who did not have surgery.

In observational studies, confounding variables may compromise a proper assessment of a result of a clinical research trial. Confounding occurs when a difference in the outcome (or lack thereof) between treated and untreated subjects can be explained entirely or partly by imbalance of other causes of the outcome in the compared groups. Potential confounders may thus effect a validity of observational studies.

Accordingly, there is a need for improved implementations of observational approaches for evaluating effectiveness of various treatments.

SUMMARY

Advantageously, the present disclosure provides solutions to the above-identified and other shortcomings in the art. Thus, in some embodiments, the systems and methods described herein allow predicting and evaluating an effect of an event (e.g., medication, treatment, etc., sometimes collectively referred to as a "treatment" herein) on a patient and/or a patient's condition. This is performed by identifying "matching" treatment and control groups or cohorts that include subjects that are similar in terms of clinical and other characteristics that influence a decision to prescribe a certain treatment. The degree to which the treatment and control groups are similar to one another, a size of the groups, and other characteristics, can be adjusted such that the treatment and control groups can be selected based on desired goals of a clinical trial.

The described systems and methods allow evaluating a patient's progress and/or survival based on the treatment and the time when the treatment was administered. For example, the effect of an anti-cancer treatment on a patient having cancer can be evaluated by comparing treatment and control groups selected for this evaluation.

In some embodiments, an interactive tool, or a dashboard, is provided that allows direct comparison of treatment and control groups based on adjusting a propensity value threshold, including identifying differences in survival among the treatment and control groups. The propensity value threshold is used to tune the propensity scoring model such that subjects assigned propensity scores that satisfy the propensity value threshold are selected for survival analysis and visualization. The effectiveness of a treatment can be evaluated by comparing a survival estimate of patients who were administered the treatment with patients who were not administered the treatment but have similar characteristics to those who received the treatment.

As mentioned above, in observational studies, it may be challenging to compare the control and treatment groups because of confounding variables. The present invention allows identifying a control cohort or group with an improved precision and more meaningful similarity to a treatment cohort or group, such that more robust comparison between the treatment and control groups is feasible. The selected control group may be referred to as a "synthetic" control group that is selected for a certain study of an effect of a medication, treatment, or another event, and given the properties of a corresponding contrasted treatment group. The described tool provides a user interface that allows selecting the treatment and control groups "on-the fly," as described in more detail below. Also, the tool allows assessing patient's demographic, clinical and other characteristics that are associated with the effect of an event on a patient and/or patient's condition.

In some embodiments, a method of evaluating an effect of an event on a condition using a base population of subjects that each have the condition is provided. The evaluation of the effect of the event on the condition may include building and training a propensity scoring model that can determine a likelihood of the subject's being prescribed a treatment for the condition, at one or more points of a time period (e.g., at one or more points of the subject's clinical interaction timeline, according to a subject's medical record). The likelihood is determined in the form of a propensity score that is similar for subjects in the identified treatment and control groups. In some embodiments, the method includes determining a propensity prediction for each of a first plurality of subjects of the base population who incurred the event, and propensity prediction for a second plurality of subjects in the base population who have not incurred the event. The propensity prediction may include a prediction, for each respective subject in the first plurality of subjects, for one or more time points in a respective time period (e.g., a subject's medical record), of a probability of each of the time points being a so-called anchor point, which is the time of the event for the respective subject. In other words, the anchor point is an instance of time when the subject in the second plurality of subjects was likely to have incurred the event. In some embodiments, an anchor point, selected among the time points predicted for each of the one or more time points in the respective time period, is the time point assigned the greatest probability across the anchor point predictions. Thus, the anchor point is a point in time at which the event "would have most likely occurred" for the subject who in fact did not incur the event. At the anchor point, a subject in the control group is presumed to be most similar (in terms of clinical features or other characteristics) to one or more subjects in the treatment group.

In some embodiments, the anchor point is predicted as a time (e.g., a number of days, such as, e.g., 16-25 days) until the occurrence of the event. The anchor point is a treatment likelihood reference point that defines when the treatment would have begun for the subject. Thus, for survival analysis, the anchor point of a subject in the control group can be used as a starting point for a survival curve.

In some embodiments of the present disclosure, the first plurality of subjects are subjects who incurred the event (e.g., those who received a medication or treatment), whereas the second plurality of subjects are subjects who are likely to have incurred the event but have not incurred it. These two cohorts do not overlap. Each of the first plurality of subjects is associated with an event start date—a date at which the event first incurred (e.g., a treatment began), and each of the second plurality of subjects is associated with a single independent corresponding anchor point. The second plurality of subjects can be, for example, subjects that have clinical features similar to those of the first plurality of subjects and that, while being likely to have been prescribed a certain treatment (to incur the event which can be that treatment), were not prescribed the treatment and did not receive it at any time. It should be noted that a propensity scoring model treats subjects in a base population in the same way, regardless of their treatment assignment. Accordingly, a predicted event start date is calculated for each subject in the first plurality of subjects (treatment cohort) as well, but the actual event start date is used in further survival analysis. In some embodiments, predicted event start dates for subjects in the first plurality of subjects are used to adjust the start dates (and anchor points) for the subjects in one or both of the treatment and control cohorts.

Once the anchor point is determined for each subject in the second plurality of subjects, the described methods compare information on the first plurality of subjects to information on the second plurality of subjects, thereby evaluating the effect of the event on the first condition. The comparison can involve comparison of a survival objective of the first plurality of subjects to a survival objective of the second plurality of subjects. This can be done using, at least in part, the event start date for each respective subject in the first plurality of subjects (i.e., a time point when that subject incurred the event) and the single independent corresponding anchor point for each respective subject in the second plurality of subjects. For example, first survival curves can be generated for the first plurality of subjects (with the data aligned to the event start dates), and second survival curves can be generated for the second plurality of subjects (with the data aligned to the determined anchor points), and the first and second survival curves can be displayed in a format suitable for assessment of the effect of the event on the first condition and on survival.

In some embodiments, the propensity predictions are generated using a propensity scoring model, also referred to herein as a propensity model. The propensity model is a machine-leaning model that is trained on the base population of subjects (or on another population of subjects), based at least in part on a plurality of features, which can be temporal or static. Various demographic, genomic, and clinical features can be selected for building a propensity model, which can be done automatically and/or manually. In some embodiments, the propensity model is applied to the base population of subjects to identify a patient profile for patients who are likely to incur the event (e.g., to receive a treatment).

In some embodiments, clinical information may be based upon fields that have been entered into an electronic medical record (EMR) or an electronic health record (EHR) by a physician, nurse, or other medical professional or representative. Other clinical information may be curated from other sources, such as molecular fields from genetic sequencing. Sequencing may include next-generation sequencing (NGS) and may be long-read, short-read, or other forms of sequencing a patient's genome. Comprehensive collections of features in additional feature modules may combine a variety of features together across varying fields of medicine that may include diagnoses, responses to treatment regimens, genetic profiles, clinical and phenotypic characteristics, and/or other medical, geographic, demographic, clinical, molecular, or genetic features. For example, a subset of features may be molecular data features, such as features derived from RNA and DNA sequencing, pathologist review of stained Hematoxylin & Eosin (H&E) or immunohistochemistry (IHC) slides, and further derivative features obtained from the analysis of the individual and combined results. Features derived from DNA and RNA sequencing may include, e.g., genetic variants which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology features. In some embodiments, features derived from structured, curated, or electronic medical or health records may include clinical features such as diagnosis, symptoms, therapies, outcomes, patient demographics such as patient name, date of birth, gender, ethnicity, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates to any of the above. Features may be derived from information from additional medical- or research-] based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data may include reports associated with a stained slide, size of tumor, tumor size differentials over time including treatments during the period of change, as well as machine learning approaches for classifying PDL1 status, HLA status, or other characteristics from imaging data.

In some embodiments, a computer-implemented method of evaluating an effect of an event on a first condition using a base population of subjects that each have the first condition is provided. The method comprises (A) obtaining a propensity value threshold; (B) identifying a first plurality of subjects in the base population and a start date of an event for each respective subject in the first plurality of subjects at which the respective subject incurs the event; and (C) using a propensity scoring model to select a second plurality of subjects from the base population, wherein the second plurality of subjects are other than the first plurality of subjects. The using (D) is done by performing a first procedure that comprises, for a respective subject in the base population: (i) applying a corresponding plurality of features for the respective subject in the base population to the propensity model tuned to the propensity value threshold, wherein a first subset of the corresponding plurality of features for which data was acquired for the respective subject is associated with a respective time period and a second subset of the corresponding plurality of features for which data was acquired for the respective subject are static, the applying (i) thereby obtaining one or more anchor point predictions for the respective subject, wherein each anchor point prediction is associated with a corresponding instance of time in the respective time period and includes a probability that a corresponding instance of time is a start date for the event for the respective subject, and (ii) assigning an anchor point for the respective subject to be the corresponding instance of time that is associated with the anchor point prediction that has the greatest probability across the anchor point predictions.

The method also includes determining a survival objective of the first plurality of subjects and a survival objective of the second plurality of subjects using the event start date for each respective subject in the first plurality of subjects and the anchor point for each respective subject in the second plurality of subjects to evaluate the effect of the event on the first condition.

Other embodiments are directed to systems, portable consumer devices, and computer readable media associated with the methods described herein. Any embodiment disclosed herein, when applicable, can be applied to any aspect of the methods described herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 5A, 5B, 5C and 5D are diagrams collectively illustrating an example of a user interface of a tool for evaluating an effect of an event on a condition, in accordance with some embodiments of the present disclosure.

FIGS. 6A, 6B, and 6C are diagrams collectively illustrating another example of a user interface of a tool for evaluating an effect of an event on a condition, in accordance with some embodiments of the present disclosure.

FIGS. 9A and 9B are diagrams collectively illustrating an example of a user interface of a tool for evaluating an effect of an event on a condition, where a low propensity value threshold is obtained, in accordance with some embodiments of the present disclosure.

FIGS. 10A and 10B are diagrams collectively illustrating the user interface of FIGS. 9A and 9B where a mid-range propensity value threshold is obtained, in accordance with some embodiments of the present disclosure.

Like reference numerals refer to corresponding parts throughout the several views of the drawings, in accordance with some embodiments of the present disclosure.

DETAILED DESCRIPTION

The present disclosure provides systems and methods for evaluating effect of an event on a condition that use a propensity model for matching and comparison of subjects that received a particular treatment with subjects who did not receive the treatment, but were likely to have been prescribed that treatment given their characteristics (e.g., demographic, therapeutic, phenotypic, genomic characteristics, etc.). The provided techniques thus allow to "match" a cohort of patients who received a certain treatment to a cohort of patients who did not receive that treatment but are likely to have been prescribed it.

In some embodiments, a propensity scoring model is trained to predict a likelihood of a subject's being prescribed a treatment, at one or more points of that subject's clinical interaction timeline. The trained propensity model is used to determine a "propensity score" that is used, in conjunction with a propensity value threshold, to identify a "treatment" cohort or group of subjects and a "control" cohort or group of subjects that are similar to each other from the perspective of the likelihood of being prescribed and administered a treatment. Thus, the subjects in the control and treatment cohorts can have similar demographic, clinical, genotyping, and other characteristics. The propensity value threshold can be used to tune a propensity scoring model. The "tuning" as used herein indicates that the output of the propensity scoring model is compared to the propensity value threshold, which may be user-selected.

In embodiments of the present disclosure, an interactive computer-implemented tool, or a dashboard, is provided that allows identifying treatment and control groups in a population of subjects based on a propensity value threshold, and for direct comparisons between the treatment and control groups. The comparison can be done using survival objective analysis (e.g., Kaplan-Meier curves), distribution of various subject features (which can be static or temporal), and pre- and post-treatment differences between the subjects in the treatment and control groups (e.g., other treatments given, prior medications, etc.).

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Figure 1:
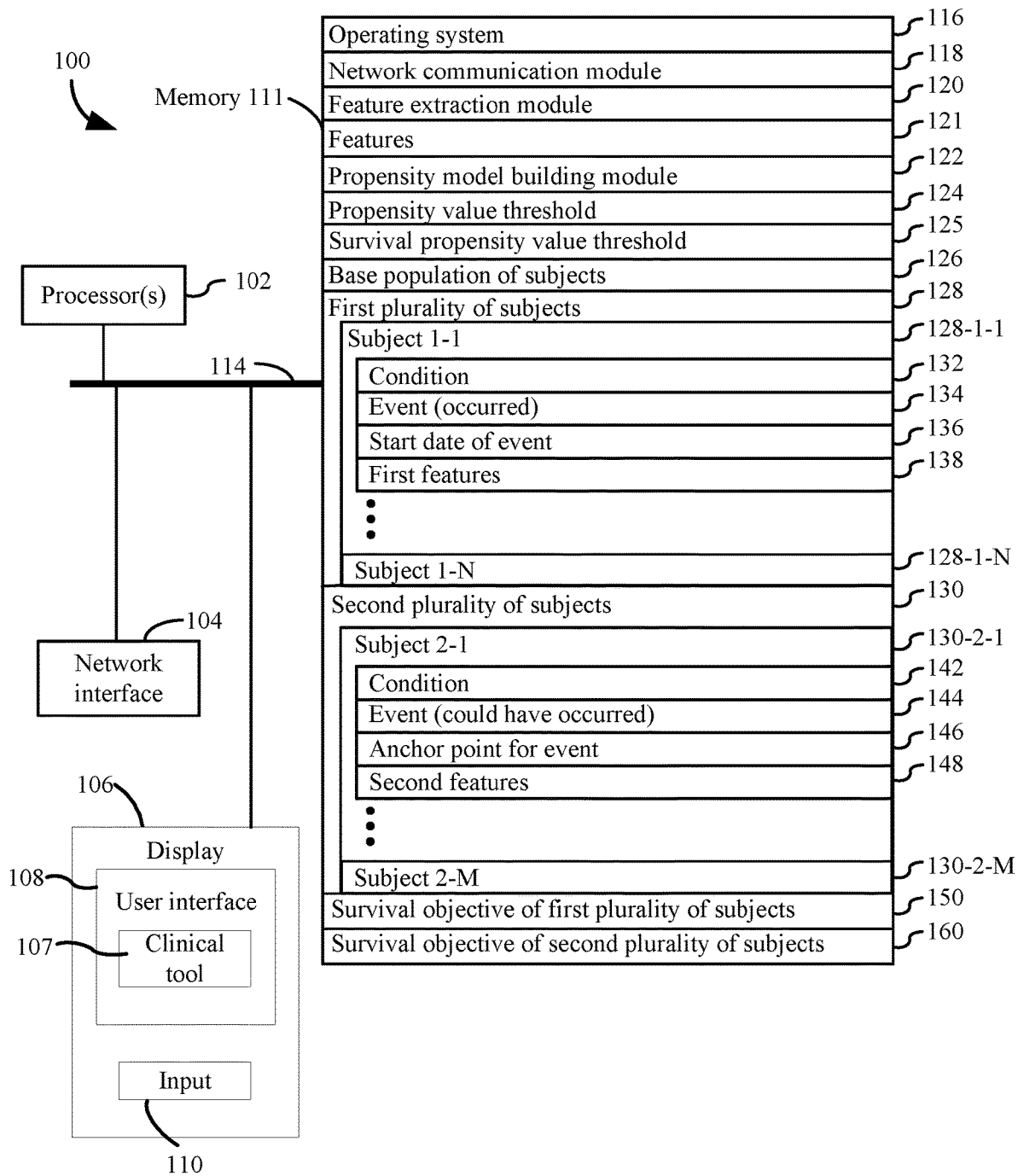
FIG. 1 is a block diagram illustrating an example computing device, in accordance with some embodiments of the present disclosure.

Details of an exemplary system are described in conjunction with FIG. 1. FIG. 1 is a block diagram illustrating a system 100 in accordance with some implementations. The system 100 in some implementations includes one or more hardware processing units CPU(s) 102 (also referred to as processors), one or more network interfaces 104, a display 106 configured to present a user interface 108, and an input system 110, a memory 111 (which can be persistent and/or non-persistent), and one or more communication buses 114 for interconnecting these components. As also shown in FIG. 1, the display 106 can also present, on its user interface 108, a user interface of a clinical tool or dashboard 107 that is configured to implement embodiments of the present disclosure, as discussed in more detail below. The one or more communication buses 114 optionally include circuitry (sometimes called a chipset) that interconnects and controls communications between system components. In some embodiments, the memory 111 is persistent, and the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory may optionally include one or more storage devices remotely located from the CPU(s) 102. In some embodiments, the memory 111 can also be implemented as a non-persistent memory, and it may include high-speed random access memory, such as DRAM, SRAM, DDR RAM, ROM, EEPROM, flash memory. The persistent memory and the non-volatile memory device(s) within the persistent memory comprise non-transitory computer readable storage medium.

In some implementations, the memory 111 can alternatively be referred to as a non-transitory computer-readable storage medium and the memory 111 stores the following programs, modules and data structures, or a subset thereof:

an optional operating system 116, which includes procedures for handling various basic system services and for performing hardware dependent tasks;

an optional network communication module (or instructions) 118 for connecting the system 100 with other devices and/or a communication network 104;

a feature extraction module 120 that is configured to extract features from various types of data related to subjects;

features 121 which can be stored in a suitable storage device;

a propensity model building module 122 configured to generate, update, and store at least one propensity scoring model, wherein the module 122 can store out of sample prediction from various models;

a propensity value threshold 124 (selectable, e.g., via a user interface of the dashboard 107);

a survival propensity value threshold 125 (selectable, e.g., via a user interface of the dashboard 107);

a base population of subjects 126 comprising a plurality of subjects from which a first plurality of subjects 128 and a second plurality of subjects 130 can be identified using a propensity scoring model built by the propensity model building module 122;

the first plurality of subjects 128 (subjects 128-1-1, ..., 128-1-N), wherein a representative subject 128-1-1 is associated with a condition 132 (e.g., a medically diagnosed physical disease such as cancer or a medically diagnosed mental disease), an event 134 (e.g., a medication or treatment such as a procedure or therapy) which occurred, a start date 136 of the event, and features 138 referred to herein as first features, which can be temporal and/or static;

the second plurality of subjects 130 (subjects 130-2-1, ..., 130-2-M), wherein a representative subject 130-2-M is associated with a condition 142 (e.g., a medically diagnosed physical disease such as cancer or a medically diagnosed mental disease), an event 144 (e.g., a medication or treatment such as a procedure or therapy) which could have occurred, an anchor point 146 for the event, and features 148 referred to herein as second features, which can be temporal and/or static;

a survival objective information 150 (e.g., survival curve information) of the first plurality of subjects 128 that is determined using the event start date 136 for each respective subject in the first plurality of subjects 128; and a survival objective information 160 (e.g., survival curve information) of the second plurality of subjects 130 that is determined using the anchor point 146 for each respective subject in the second plurality of subjects 130.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system other than the computer system 100 and that is addressable the computer system 100 so that the system 100 may retrieve all or a portion of such data when needed.

It should be appreciated that FIG. 1 depicts the system 100 as a functional description of the various features of the present disclosure that may be present in computer systems.

As a person of skill in the art would understand, some of components and modules shown separately can be combined in a suitable manner. Also, although FIG. 1 depicts certain modules in the non-persistent memory 111, some or all of these modules may instead be stored in a persistent memory or in more than one memory. For example, in some embodiments, the base population of subjects 126 may be stored in a remote storage device which can be a part of a cloud-based infrastructure. Any other components can be stored on remote storage device(s).

Figure 2:
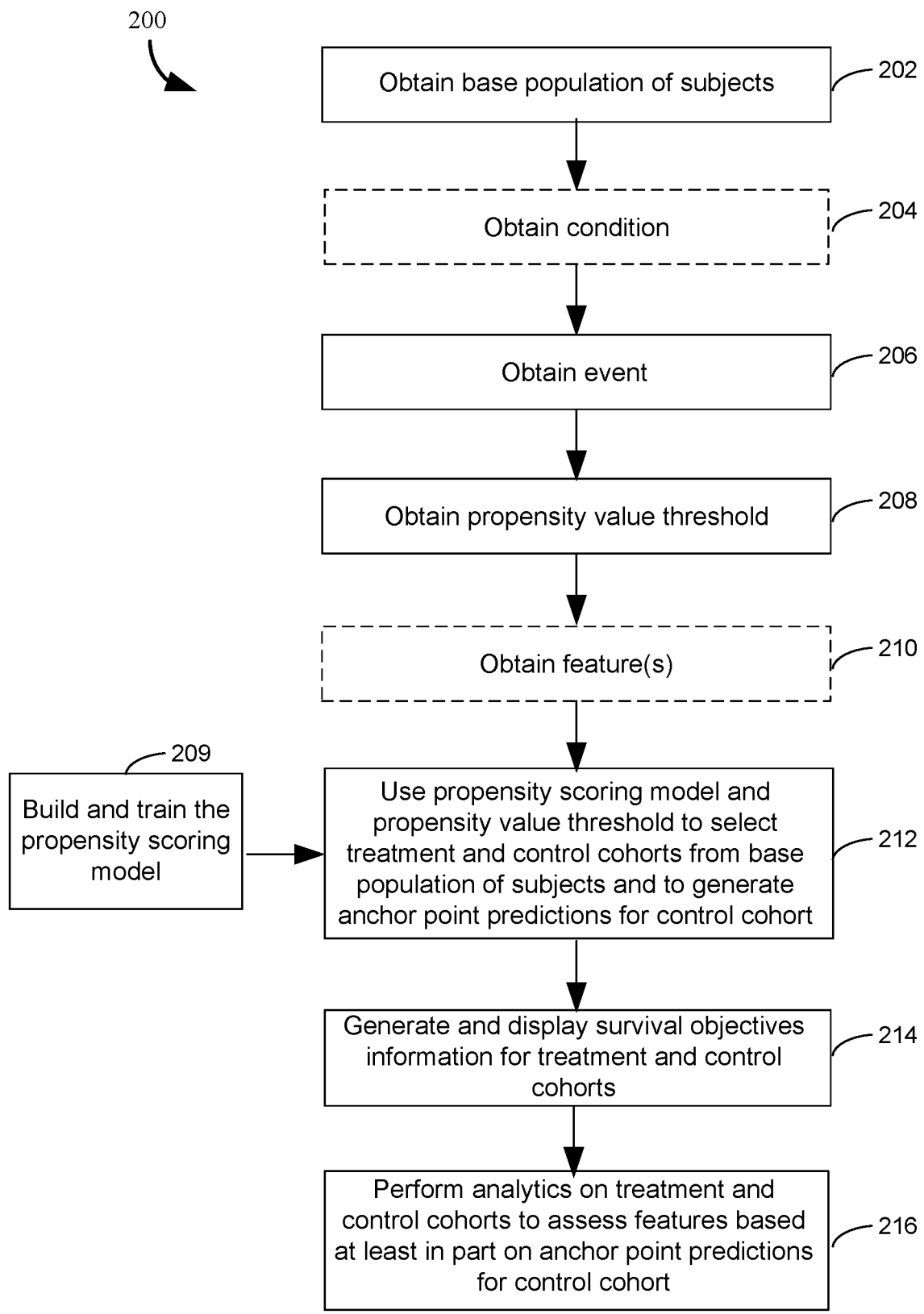
FIG. 2 is a flow chart illustrating a process of evaluating an effect of an event on a condition, in accordance with some embodiments of the present disclosure.

FIG. 2 illustrates a process 200 of evaluating an effect of an event on a condition (e.g., an effect of a medication or treatment on a diagnosed conditioned such as cancer), which can be implemented in the system 100 (FIG. 1) or in another suitable system configured to execute the tool 107. The process 200 can start, for example, when a clinical tool for evaluating the effect of an event on a condition is initiated or in response to any other trigger. As shown in FIG. 2, at block 202, a base population of subjects (e.g., the base population of subjects 126 of FIG. 1) can be obtained, which can be done in a number of ways. For example, with reference to FIG. 3 which illustrates schematically a user interface 307 of the tool 107, a base population of subjects can be obtained based on user input received via a user interface element 302 of the user interface 307. In the example illustrated in FIG. 3, the user interface element 302 is shown as a drop-down menu element from which a source of information on the base population of subjects can be provided by a user. It should be appreciated, however, that the base population of subjects can be obtained in other ways.

Regardless of the way in which it is obtained, the base population of subjects can include subjects that have a certain condition such that all of the subjects have that condition. In some embodiments, however, the base population has subjects that have different conditions or different types of conditions. For instance, the base population of subjects can have subjects with different types of cancer or different types of a mental disease. Thus, FIG. 2 shows that, at optional block 204, a condition can be obtained such that only the subjects having the obtained condition are considered for further analysis. The condition can be obtained, for example, via the user interface 307 of FIG. 3, for example, via the user interface element 302 or via another user interface element configured to receive user input. In some embodiments, however, the processing at block 204 is omitted since the base population can be defined as a population in which each subject has a certain condition (e.g., cancer). Each subject in the base population can also be associated with other features related to the condition—e.g., a type and/or stage of cancer. In general, the base population can be any type of a collection of patient's information stored in patients' medical records or in another manner. The information can be updated as the patient (also referred to as a subject herein) is being monitored.

Figure 3:
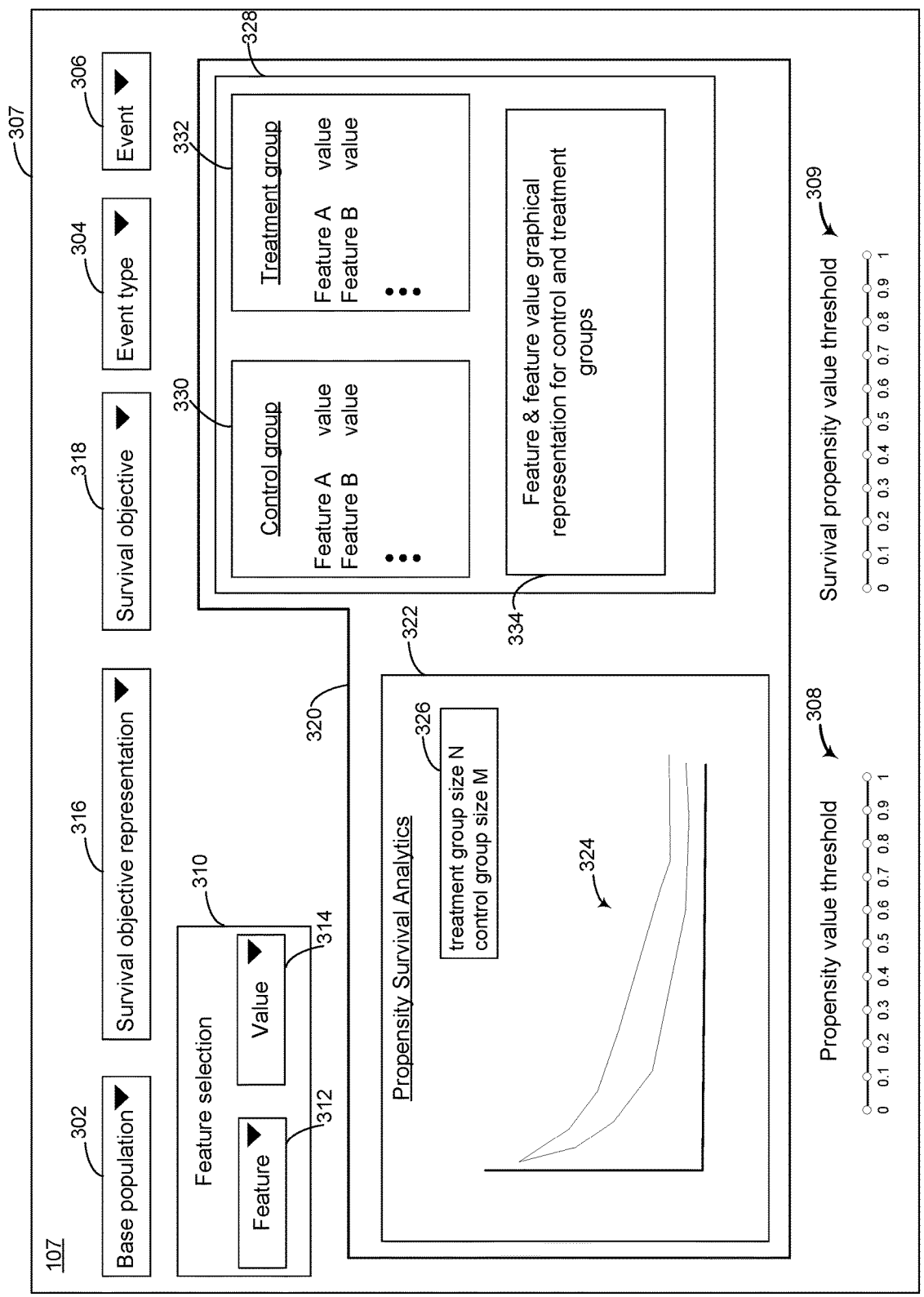
FIG. 3 is a diagram illustrating an example of a user interface of a tool for evaluating an effect of an event on a condition, in accordance with some embodiments of the present disclosure.

Further, at block 206 of FIG. 2, an event, such as a medication, procedure, or treatment (sometimes collectively referred to herein as a "treatment"), is obtained. In some embodiments, information on the event can be acquired via the user interface 307 presenting elements of the tool 107. For example, as shown in FIG. 3, the event can be obtained via an event type user interface element 304 and via an event user interface element 306. The event type user interface element 304 can be used to acquire an event type such as, for example, a medication, treatment, therapy or any other type of event can affect a subject's condition. The event user interface element 306 can be used to receive a selection of a specific event of a certain type. As an example, the event type can be a medication and the event can be fluorouracil.

At block 208 of FIG. 2, a propensity value threshold can be obtained. FIG. 3 shows by way of example that the propensity value threshold can be obtained via a user interface element 308. In some embodiments, the propensity value threshold comprises a propensity value range which can be, e.g., a range of between 0 and 1, as shown in the example of FIG. 3. In this example, the user interface element 308 is a slider which can be adjusted based on a user input such that a desired range is selected. It should be appreciated, however, that the user interface element 308 can be any other element that allows receiving user input indicating a selection of a propensity value threshold. It should also be appreciated that the processing in FIG. 2 is shown in the particular order by way of example only. Thus, in some embodiments, building and training a propensity model may occur separately and prior to obtaining the propensity value threshold at block 208. For example, in some embodiments, the trained propensity model may be stored in advance.

Regardless of the specific way in which the propensity value threshold is obtained, information on different subjects from the treatment and control groups can be used for survival and other types of analysis. In particular, only the subjects assigned a respective propensity score that satisfies the currently selected propensity value threshold are included in the analysis, and, if a different propensity value threshold is obtained, different subjects from the treatment and control groups can be selected for further analysis.

In addition to receiving a selection of a propensity value threshold, in some embodiments, as shown in FIG. 3, the tool 107 can be configured to receive an expectations threshold. This can be done, for example, via the user interface 307, and a user interface element 309 (a slider, in this example) is shown in FIG. 3. The user interface element 309 can be used to receive a selection regarding a survival propensity value threshold (e.g., a threshold range or value indicating a likelihood to progress or another survival objective), which is also referred to herein as an expectations threshold. In this way, a user may have additional control over expectation survival analysis, in combination with the propensity modeling. For example, cohort selection may be narrowed down to patients that are similarly likely to progress or survive, for both control and treatment groups, while maintaining the current visualization of the effects of the treatment. For example, randomized, controlled clinical studies have demonstrated that Erlotinib (Tarceva, a small-molecule, orally dosed, anti-cancer drug that inhibits the epidermal growth factor receptor) significantly improved survival in patients with previously treated non-small-cell lung cancer. Erlotinib may be given to lung cancer patients who have an EGFR mutation, including those patients who are at cancer Stage III or IV. In some embodiments, treatment propensity would identify differences between the patient based on whether or not they were administered the treatment. However, Stage III patients would have different baseline survival profiles than Stage IV patients. Thus, resulting survival curves for control and treatment groups may be skewed with respect to each other, depending on a proportion of Stage IV in each group. Thus, providing a way for a user to select a survival propensity threshold for visualization of the survival expectations advantageously allows the user to further refine selection of the treatment and control cohorts, by narrowing the selection of patients to those who are just as likely to progress/survive across the control and treatment cohorts. This provides a benefit to the user by matching automatically on prognostic factors in addition to the treatment factors, e.g., in cases where the patients included in each cohort have differences in expected survival. For example, with reference to the Erlotinib example above, using both propensity value and survival propensity thresholds allows accounting for special characteristics present in a cohort of patients with non-small-cell lung cancer who are receiving late-stage treatments including Erlotinib.

In some embodiments, as shown at block 210 of FIG. 2, one or more features can be selected for constructing a propensity scoring model. In some embodiments, features for the building and training the model are selected prior to the use of the model by the user.

For example, for each patient, information from the patient's medical records may be received, which may be information associated with multiple time points (e.g., doctor visits, treatments, or any other events on the patient's timeline involving interactions with a medical care provider). A patient's timeline may extend, for example, from a condition or disease diagnosis to the current time or patient's death. Events related to patient's interactions with a medical care provider can be grouped into time points, such as specific dates. For instance, examples of information in a medical record for a patient A having a tumor can be:

date of biopsy collection, Jul. 1, 2018 (KRAS PL1S147GLU mutation with high SNP effect identified);
start medication A, Aug. 1, 2018;
procedure performed, Nov. 1, 2018;
therapy outcome reported—progression, Jan. 1, 2019; and
imaging performed, Jul. 1, 2018 and Nov. 1, 2018.

Accordingly, four time points can be identified for patient A:

Patient A: Jul. 1, 2018;
Patient A: Aug. 1, 2018;
Patient A: Nov. 1, 2018;
Patient A: Jan. 1, 2019.

Features may be determined for patient A, such as, e.g., a time since starting a medication (e.g., medication A), a last time since taking a medication, a time since last progressive therapy outcome (a patient's response to a medication), a largest tumor size to date/last recorded tumor size, a time since metastasis, the most severe effect of identified SNP (low effect, high effect), and RNA and DNA features (expression level per gene/transcript, which may require additional processing to reduce dimensionality of feature space). It should be appreciated that the features may include any of the features described herein, or any other features.

Continuing with the example of patient A, a state of each of the determined features may be identified for each of the four time points, for example, as follows:

Patient A: Jul. 1, 2018:
Time since Starting Medication A: null
Time since Last Imaging: 0 days
Highest SNP Effect As Identified by Lab A: Germline: KRAS: High (5)
Patient A: Aug. 1, 2018:
Time since Starting Medication A: 0 days
Time since Last Imaging: 1 month
Highest SNP Effect As Identified by Lab A: Germline: KRAS: High (5)
Patient A: Nov. 1, 2018:
Time since Starting Medication A: 3 months
Time since Last Imaging: 0 days
The effect of the most deleterious variant in the gene on the protein product created by that gene as identified by Lab A: Germline: KRAS: High (5)
Patient A: Jan. 1, 2019
Time since Starting Medication A: 5 months
Time since Last Imaging: 2 months
Highest SNP Effect As Identified by Lab A: Germline: KRAS: High (5)

In various embodiments, features can be qualitative and quantitative. Some features can be binary. Also, some features may not have specific values associated with them.

Non-limiting examples of features include features related to Karnofsky Performance Status; menopausal status (menopausal, postmenopausal, missing); smoker status (current, ex-smoker, never smoker, non-smoker, missing); a number of prior distinct cancers; a number of days since a first diagnosis of carcinoma of the ampulla of Vater, anus cancer, cancer of appendix, cancer of biliary tract, bone cancer, brain cancer, breast cancer, cervical cancer, colon cancer, cancer of a digestive organ, endometrium cancer, cancer of esophagus, cancer of fallopian tubes, cancer of a female genital organ, head and neck cancer, kidney cancer, larynx cancer, liver cancer, lung cancer, lymphoid, hemopoietic and/or related tissue cancer, cancer of meninges, ovary cancer, pancreas cancer, peritoneum cancer, prostate cancer, cancer of rectosigmoid junction, rectum cancer, respiratory tract cancer, cancer of skeletal system, skin cancer, trunk skin cancer, small intestine cancer, cancer of soft tissues, stomach cancer, thyroid cancer, tongue cancer, unknown site cancer, urinary and/or bladder cancer, uterus cancer, vulva cancer; a number of days since a last occurrence of abnormal findings based on diagnostic imaging of breast cancer, administration of antineoplastic agent, anemia, dehydration, disorder of bone, disorder of breast, dyspnea, essential hypertension, estrogen receptor assay, fatigue, imaging of thorax indicating abnormal findings, advised immunization, long-term current use of drug therapy, osteoporosis, past history of a certain procedure, a pedal cycle accident, screening for malignant neoplasm of breast, chronic obstructive lung disease, type 2 diabetes mellitus; age at an event; age group; gender; race (African, American Indian or Alaska Native, Asian or Pacific Islander, Asian, Black or African American, Caucasian, etc.); a number of days since a first encounter of accident and emergency service, a first encounter of admission to a hospice, a first encounter of an advance care planning by the physician or other qualified health care professional (e.g., first 30 minutes), a first encounter of an after-surgery follow-up visit, a first encounter of anti-clotting management for a patient taking a blood thinner (first 90 days of therapy), a first counter of clinical oncology service, a first encounter of a critical care delivery to a critically ill or injured patient (e.g., first 30 to 74 minutes), a first counter of an emergency department visit (a problem of high severity or a problem with significant threat to life or function), a first counter of an emergency room admission, a first counter of an established patient office or other outpatient visit, etc.; a number of days since a last encounter of accident and emergency service, a last encounter of admission to a hospice, a last encounter of an after-surgery follow-up visit, a last encounter of clinical oncology service, a last encounter of emergency room admission, a last encounter of hospital admission, a last encounter of a patient encounter procedure, a last encounter of a patient office consultation, a last encounter of being seen in a hospital outpatient department, etc.; a status of a lab test (albumin, basophils, calcium, chloride, erythrocyte, glucose, hematocrit, hemoglobin, leukocytes, lymphocytes, monocytes, neutrophils, platelets, potassium, protein, sodium, urea nitrogen (e.g., average or last values)); a number of days or months since receiving a certain medication; a number of prior distinct metastases; a number of days since a first metastasis (e.g., of abdominal lymph node, adrenal gland, bone, bone marrow, brain, genital organ, large intestine, liver, lung, lymph node, lymph node of thorax, mediastinal lymph node, mediastinum of nervous system, omentum, ovary, pelvic lymph node, pelvis, peritoneum, pleura, pleural cavity, etc.); a number of days since a last occurrence of a procedure; a number of days since a last occurrence of active surveillance of a certain procedure (e.g., appendectomy, aspiration and/or injection of large joint or joint capsule, bilateral mastectomy, bilateral salpingectomy with oophorectomy, biopsy of breast, biopsy of large bowel using an endoscope, block dissection of mediastinal lymph nodes, cholecystectomy, colectomy, collection of blood specimen from a completely implantable venous access device, contralateral prophylactic mastectomy, excision of axillary lymph node, excision of breast tissue, excision of group of lymph nodes, excision of lesion of brain tissue, excision of periaortic lymph nodes, excision of sentinel lymph node, excisional biopsy, insertion of needle into vein for collection of blood sample, interventional debulking surgery, lobectomy of lung, local excision, low anterior resection of rectum, mastectomy of left breast, mastectomy of right breast, modified radical mastectomy, omentectomy, pancreaticoduodenectomy, partial mastectomy, partial omentectomy, partial resection of colon, pelvic lymphadenectomy, preoperative placement of needle localization wire in breast, puncture of skin for collection of blood sample, radical prostatectomy, reexcision, removal of appendix, removal of gallbladder, salpingo oophorectomy, sequencing specimen collection, sigmoid colectomy, surgical procedure, thoracoscopic lobectomy of lung, total abdominal hysterectomy, transurethral resection of bladder neoplasm, tumor surgically unresectable, etc.); a number of days since a first radiotherapy; a status regarding a biochemical recurrence; a number of days since a last recurrence of a certain cancer; results of fluorescence in situ hybridization (for ALK, ATM, BCR, BRCA1, BRCA2, CCND1, CDKN2C, CKS1B, EGFR, ERBB2, ESR1, EWSR1, FGFR3, IGH, KMT2A, MAF, MDM2, MET, MYC, PGR, PTEN, RB1, RET, ROS1, and TP53 genes); results of a gene copy analysis (e.g., for any one or more of the above-mentioned genes, or other genes); results of a gene mutation analysis; results of a gene rearrangement analysis; results of a gene immunohistochemistry analysis; a number of days since a last occurrence of a therapy change for a certain reason; a number of days since a first finding of a tumor (e.g., for various types and/or stages of tumor); and any other features.

It should be appreciated that the processing at blocks 204-210 of FIG. 2 can be performed in any suitable order and that the specific order is shown in FIG. 2 by way of example only. It should also be appreciated that some or all of the obtaining at blocks 204-210 can be performed in ways other than based on user input acquired via elements of a user interface. Thus, in some embodiments, the obtaining at blocks 202-210 can be performed automatically. For example, in some embodiments, a propensity value threshold can be selected by the processor based on features of the subjects in the base population. Additionally or alternatively, in some implementations, the propensity value threshold can be suggested to the user via the user interface.

At block 212 of FIG. 2, a propensity scoring model and the propensity value threshold obtained at block 208 may be used to select treatment and control cohorts from the base population of subjects and to generate anchor point predictions for each subject in the control cohort. As shown in FIG. 2, the propensity scoring model can be built and trained at block 209, and at block 212 the model can be refined. The treatment cohort is also referred to herein as a first plurality of subjects (e.g., first plurality of subjects 128 of FIG. 1) and the control cohort is also referred to herein as a second plurality of subjects (e.g., second plurality of subjects 130 of FIG. 1).

The propensity scoring model may be configured to determine a propensity score for each subject in the base population. The propensity score can be defined as the probability of receiving an active treatment (Z=1 vs. Z=0), conditional on the observed baseline covariates (X):

$$e_i = \text{Prob}(Z_i = 1 | X_i) \quad (1)$$

The $e_i$ value describes the probability for a patient i having the active treatment. Propensity scores are described, for example, in Austin, *The use of propensity score methods with survival or time-to-event outcomes: reporting measures of effect similar to those used in randomized experiments*, Statistics in Medicine (2013), 33:1242-1258, and Rosenbaum & Rubin, *The central role of the propensity score in observational studies for causal effects*, Biometrika (1983), 70(1):41-55, each of which is incorporated by reference herein in its entirety. This score acts as a balancer—conditional on the propensity score, the distribution of X should be identical between the treatment and control groups. A model that links a binary response to a set of features can be used. See Stuart, *Matching methods for causal inference: a review and a look forward*, Statistical Science (2010) 25(1): 1-21. In some embodiments the propensity model is a non-parametric model. In some embodiments the propensity model is a boosted CART model a generalized boosted model, or a greedy nearest neighbor matching model.

In some embodiments, a propensity score, generated using the propensity scoring model for each subject in the treatment cohort and each subject in the control cohort, is compared to the propensity value threshold. As a result, only the subjects associated with respective propensity scores that meet the propensity value threshold (e.g., that are within a certain range when the propensity value threshold is defined as a range, or that are above or below the threshold) are selected for the subsequent analysis and visualization.

For instance, continuing with the example of patient A above, one or more propensity targets may be defined for patient A. For example, the propensity targets may include a probability of being administered a medication X for first time in 16-25 days (P1), a probability of being administered a procedure Y for first time in 16-25 days (P2), and a probability of being administered radiotherapy Z for first time in 16-25 days (P3). It should be noted that the time span of 16-25 days is described by way of example only, as any other time range may be used alternatively. A propensity model may be applied to generate propensity predictions for every target (P1, P2 and P3) at every time point in a patient's timeline. It should be appreciated that, although this example describes propensity predictions for patient A only, the propensity predictions are generated for each of the patients in the treatment and control groups. The generated propensity predictions can be compared to a propensity value threshold (obtained, e.g., at block 208 of FIG. 2), and the generated propensity predictions having values that satisfy the propensity value threshold can be used for constructing survival curves and other types of survival objectives information for treatment and control groups.

In some embodiments, the treatment cohort can be different from the control cohort such that these cohorts do not overlap. The treatment and control cohort can be of the same size, or they can have different sizes. As mentioned before, the treatment cohort includes subjects (having the condition) that incurred the event (e.g., received a treatment as defined above), and each subject in the treatment cohort is therefore associated with a start date of an event at which that subject incurred the event. The control cohort includes subjects (having the condition) that could have incurred the event but did not incur the event.

As an example, the drug cisplatin has been approved by the U.S. Food and Drug Administration (FDA) as an established combination therapy with cyclophosphamide in patients with metastatic ovarian tumors who have already received appropriate surgical and/or radiotherapeutic procedures. Thus, as an example, a treatment cohort may be defined as a cohort of a patients with metastatic ovarian tumors who received the combination therapy of cisplatin and cyclophosphamide after receiving appropriate surgical and/or radiotherapeutic procedures. The control cohort may be defined as a cohort of patients who did not receive the combination therapy of cisplatin and cyclophosphamide after receiving appropriate surgical and/or radiotherapeutic procedures. Exemplary methods for defining the treatment cohort and control cohort are described below.

In some embodiments, the method in accordance with embodiments of the present disclosure assigns each subject in the base population into one of the first plurality of subjects, the second plurality of subjects, or a group of non-matching subjects that are not assigned to the first plurality of subjects or the second plurality of subjects. A subject is assigned to the first plurality of subjects or to the second plurality of subjects based on a propensity score determined for that subject. Subjects in the first and second plurality of subjects have similar propensity scores such that the subjects have similar probabilities of being administered a treatment or medication given the subjects' respective features.

In some embodiments, the propensity scoring model is used at block 212 by applying a corresponding plurality of features for the respective subject in the base population to the propensity scoring model tuned to the propensity value threshold. In some embodiments, at least some of the plurality of features can be selected via the user interface 307. The plurality of features can include a first subset of features each of which is associated with a respective time period (e.g., the subject's clinical interaction timeline for which data exist), and a second subset of features that are static. The propensity scoring model is applied such that, for each subject in the control cohort, one or more anchor point predictions are generated. Each anchor point prediction is associated with a corresponding instance of time in the respective time period and includes a probability that the instance of time is a start date for the event for the respective subject in the control cohort. Thus, the anchor point predictions include predictions, within the respective time period, for when the event could have been started (but did not start) for the subject in the control cohort. An instance of time that is associated with an anchor point prediction that has the greatest probability across the anchor point predictions is taken as the anchor point for the subject, which is the time when the subject could have incurred the event. For example, it is a time when the subject could have been prescribed a medication or treatment, identified based on the subject's similarity to subjects who were indeed prescribed and received the medication or treatment.

In some embodiments, a propensity scoring model is generated as a cross-validated model (e.g., random forest, gradient boosting, linear or logistic regression, a neural network, etc.) with a treatment as the outcome and with certain features as predictors. In some embodiments, the cross-validation can be performed on the entire base population. The features for the model can be selected automatically or manually, and, in some embodiments, the feature selection process may involve missing value imputation. Out-of-fold predictions returned by the propensity scoring model can be saved and used for future predictions. The propensity scoring model can assign a subject from the base population to one of the control and treatment groups. In some embodiments, each subject assigned to the treatment group is associated with an event start date at which the subject first incurred the event (e.g., a medication or procedure), and each subject assigned to the control group is associated with an anchor point which is a date at which the subject could have first incurred the event (e.g., a medication or procedure). In addition, in some embodiments, one or more of the subjects from the base population of subjects are not assigned to either the treatment or control group, which can occur for various reasons, e.g., the subjects have certain outlier features, the subjects a large number of missing appointments (such that a subject's medical record has a number missing values above a certain threshold), etc. Information on a subject assigned to a control group will be excluded from further analysis if the propensity value calculated for that subject is outside of a certain range, such as a propensity value threshold.

In some embodiments, the control group of subjects can be selected by first removing all subjects (meaning the information such as, e.g., medical records of the subjects) that were assigned to the treatment group. The propensity scoring model is then applied to subjects associated with anchor point predictions having respective probabilities that are above a threshold. In this way, from the subjects that are not in the treatment group, subjects are selected who are likely to incur the event at one or more time points (instances of time), and a single anchor point (i.e., a single instance of time) that has the greatest probability across the anchor point predictions is selected for each subject.

As discussed above, an anchor point is generated for each subject in the control group. Subjects in the treatment group are assigned respective anchor points as a date at which they first received a treatment. In some embodiments, anchor points generated for subjects in the control group are adjusted (e.g., a certain number of days is added to some or all of the anchor points), to "align" subjects in the control and treatment groups at their respective anchor points. The anchor points, which may or may not be adjusted, are used as start days for survival analysis, e.g., in the form of survival curves.

In some embodiments, because one anchor per patient is chosen, for each patient remaining, only the event start date (and prediction) associated with the highest prediction that the patient received is selected. For example, in some embodiments, a likelihood of being administered a treatment is predicted for each patient event start date, and the most likely date is selected based on a point of maximum likelihood.

In some embodiments, applying the propensity scoring model to the base population comprises generating a predicted event start date for each subject in the base population, thereby determining whether or not the subject would receive a given treatment for the first time within the next X days or months (e.g., X=2 months, in an embodiment), rather than determining whether or not the subject would receive the treatment on that date.

Thus, a predicted event start date is generated for each subject, including the subjects that may be assigned to the treatment group, based on an indication in their medical records that the treatment was administered to the subjects. A date predicted for an event start date for a subject in the control group can be adjusted to generate a respective anchor point. This can be done by analyzing the distribution of difference in days between a respective predicted event start date for each subject in the treatment group with a positive outcome (meaning, e.g., they did receive the treatment within X months) and the date when that subject actually received the treatment. Then, for each of the event start dates generated for the subjects in the control group, a certain number of days is added to the event start date, following the distribution that was observed for the treatment group (e.g., from a normal distribution with the mean and standard deviation taken from the sample statistics of the treatment distribution, uniform distribution, etc.). In some embodiments, the number of days added to the event start date can be between ten days and sixty days, though any other number of days can be added.

In some embodiments, feature selection involves preprocessing of "raw" features into a feature set. As used herein, a feature set is a collection of features that occurred in a patient history before a specific date. The specific date may be selected from the current date (e.g., the date of execution and/or (re)training the model) or any date prior to the current date. The preprocessing may include reducing dimensionality of features by, e.g., binning features or using other approaches. For example, for an age feature, instead of using ages of subjects in a year format, age ranges may be used (e.g., ranges with a 10-year increment, such as resulting groups are 0-9, 10-19, 20-29, 30-39, 40-49, 50-59, 60-69, 70-79, 80-89, 90-99, and 100-109). In some instances, an additional "Unknown" group may be defined for subjects whose age is not known. In this way, the reduction from 100 (or more) data points to 11 data points can facilitate a more robust analysis. As another example of feature preprocessing, subject's gender, race, or another related characteristic may be normalized so that, e.g., subjects having different respective ethnicity may be binned into similar ethnicities. For example, a race of Caucasian may be binned with White, and/or a dataset including Japanese, Korean, and Filipino subjects may be binned into Pacific Islander or Asian. As another example, features that are entered into the record by their occurrence may be processed into respective features that are associated with a number of days since their first or last occurrence.

Referring back to FIG. 2, at block 214, the process 200 generates respective survival objectives information for treatment and control cohorts. The survival objectives are generated in the way that allows a comparison of a survival objective of the treatment cohort and a survival objective of the control cohort using the event start date for each respective subject in the treatment cohort and the anchor point for each respective subject in the control cohort, to evaluate the effect of the event on the first condition.

In some embodiments, the propensity scoring model is trained using a binary classification algorithm with the survival objective as an objective response variable. The survival objective can be, for example, a time until death, time until progression of the first condition, or time until an adverse event associated with the first condition is incurred. The survival objective can also be a survival from first diagnosis of primary cancer, survival from prescription of specific medication(s), survival from a specific diagnosis (e.g., a cancer stage diagnosis). In some embodiments, techniques described in Austin, P. *The use of propensity score methods with survival or time-to-event outcomes: reporting measures of effect similar to those used in randomized experiments*, Stat Med. 2014 Mar. 30; 33(7): 1242-1258, which is incorporated herein by reference in its entirety, can be employed for training a propensity scoring model.

As shown in FIG. 3, the user interface 307 of the tool 107 can be configured to receive user input indicating a user selection regarding how the information on the survival objectives is displayed on the user interface 307. For example, as shown in FIG. 3 by way of example only, a survival objective representation element 316 and a survival objective (type) element 318 can be configured to receive respective user input regarding a survival objective representation (e.g., survival curves) and a type of a survival objective (e.g., progression free survival, time until death, time until progression of the condition, time until an adverse event associated with the condition is incurred, etc.). Any other types of user interface elements can be configured to receive user input regarding the survival objectives for the treatment and control cohorts identified from the base population of subjects.

In FIG. 3, a results panel 320, which can include various sub-panels, illustrates schematically how results of the selecting the treatment and control cohorts and of the generating the respective survival objectives information for these cohorts can be presented. Thus, a sub-panel 322 presents propensity survival analytics comprising survival curves 324 (shown schematically) generated for the treatment and cohort groups.

As also shown in FIG. 3, the panel 320 can also include information on a size of the treatment and control groups which are shown by way of example only in a sub-panel 326, which, in turn, is shown positioned within the sub-panel 322, though it may be presented in any other location within the panel 320. It should be appreciated that the user interface elements of FIG. 3 are shown by way of example only, and that the tool that implements the described techniques can present any other user interface element, some or all of which can be interactive, and the elements can be positioned in the user interface in a suitable manner. Moreover, in some embodiments, the tool can be configured to receive a user input in a speech format or in any other format.

Furthermore, in some embodiments, the user interface 307 may be configured to allow a user to select feature(s) for propensity survival analysis. For example, as shown by way of example in FIG. 3, the user interface 307 may include a feature selection module 310 which allows for receiving user input indicating a selection of one or more features (e.g., via a user interface element 312) and respective values of one or more features (e.g., via a user interface element 314). The user interface elements 312, 314 may be drop-down menus or any other type of interactive elements. The features that can be selected can be any of the features used to build the propensity model. However, in some embodiments, the features available for user selection may be top-ranked features that contributed the most to the identification of the treatment and control cohorts within the base population. For example, in the propensity model, features can be weighted by their significance, and a certain number of most significant features may be presented via the user interface 307 for user selection. In this way, the user may be allowed to select a feature and its respective value or a range of values, depending on implementation. For example, the user can be allowed to select an age or an age group, race, stage of cancer, gender, drugs taken pre- and/or post-treatment, censorship rates, an indicator from clinical data, and any other feature. Regardless of the specific way in which selection of features and their associated values can be received via the user interface, the selection of specific features may result in an alternative survival curves 324.

In some embodiments, the survival objectives information comprises Kaplan-Meier estimates, which are the cumulative probability of surviving until time t. To calculate the Kaplan-Meier probability estimate at day 3, for example, the calculation may be $P(S1) * P(S2|S1) * P(S3|S2)$, or more generally, $P(St)=P(St|St-1) * P(St-1)$, where $P(St)$ is the probability of the subject's survival on a certain day, $P(St-1)$ is the probability of the subject's survival on a day prior to the certain day, and $P(St|St-1)$ is the probability of the subject's survival on the certain day given that the subject was alive on a day prior to the certain day. In some embodiments, the Kaplan Meier function can make the following assumptions: 1) patients who are censored have the same survival prospects as those who continue to be followed, 2) the survival probabilities are the same for subjects recruited early and late in the study, and 3) the event happens at the time specified.

In some embodiments, the panel 320 can also present results related to features that were used to identify the treatment and control cohorts based on the propensity value threshold. Features and their respective values can be presented in various ways that allow comparison of the treatment and control cohorts and assessment of features that contributed to the selection of the treatment and control cohorts. In some implementations, the features can be ranked based on the degree of their contribution to the selection of the treatment and control cohorts.

At block 216 of FIG. 2, the process 200 comprises performing analytics on various information related to the treatment and control cohorts to assess features of the subjects included in the cohort based at least in part on anchor point predictions for the control cohort. Some or all of the features can be ranked or compared otherwise. FIG. 3 shows that the panel 320 can include a features sub-panel 328 that can display features 330 for the subjects in the control group and features 332 for the subjects in the treatment group. The features can be displayed along with their values—e.g., in some embodiments, average values across all subjects in the group can be displayed. FIG. 3 illustrates by way of example that the same respective features (e.g., Feature A, Feature B, etc.) from the control group features 330 and the treatment group features 332 can be displayed alongside, which facilitates feature comparison.

As shown in FIG. 3, the features sub-panel 328 can also include a sub-panel 334 in which features and their respective values can be presented as one or more graphical representations for the control and treatment group. For example, the features displayed in the sub-panel 334 can be an age group, stage of a disease (e.g., cancer), etc., as shown in more details in examples below. It should be appreciated that the user interface 307 can present various visual representation that allow exploring clinical differences between the treatment and control groups. Examples of the representations are discussed below.

Regardless of the specific way in which the features and related information regarding the subjects in the treatment and control groups are presented, the features and other information are presented in a way that allows comparing survival objectives of the treatment and control groups to determine impact of treatment on survival. For example, demographic, geographical, clinical, genomic differences, a treating physician-related differences, and any other differences between the treatment and control cohorts are assessed. In this way, in some embodiments, patient's features/characteristics can be assessed that impact a decision to prescribe and administer a treatment to the patient. The goal is to determine, from the treatment and control cohorts that are selected to be similar, their differences that result in one cohort's being prescribed the treatment and another not being prescribed the treatment. One or more features, including shared characteristics of patients and clinical considerations, can be identified that lead to a decision to prescribe the treatment.

In some embodiments, the analytics performed on the identified treatment and control cohorts in accordance with the present disclosure can include receiving a request for treatment recommendations from a user, for instance, a physician treating a patient. For example, the tool in accordance with embodiments of the present disclosure, or a different interactive tool, can be used to receive such a request which can be associated with information on the patient (e.g., from the patient's medical record). In some embodiments, treatment recommendations may be generated in advance, regardless of whether or not any request is received. The information on the treatment and control cohorts can be used to identify, based on patient information, whether there is match among the patients in the cohorts to the patient in the physician's request. If the match is identified, the described techniques can generate an indication that certain one or more treatment options can be applicable to the patient. It should be appreciated that a treatment recommendation can be a general recommendation not pertaining to a specific patient. For example, in some embodiments, guidelines for a specific treatment (e.g., a drug) can be provided, for example, characteristics (e.g., a disease stage, hormone status, prior treatments, etc.) that are required or recommended in order to administer the treatment.

In some embodiments, treatment cohort characteristics are compared to identify final clinical considerations that lead to patients prescribed a treatment. If characteristics of a patient match the final considerations that lead to treatment, the patient can be prescribed the treatment.

In embodiments in accordance with the present disclosure, the survival objectives information for the treatment and control cohorts can be generated and displayed automatically, in response to receiving user input indicating a selection of a required number of elements and/or in response to a certain other trigger. In some embodiments, additionally or alternatively to displaying the respective survival objectives information for the treatment and control cohorts, the survival objective information for the treatment and control cohorts can be stored, in a suitable format, in memory of a computing device.

Figure 4A:
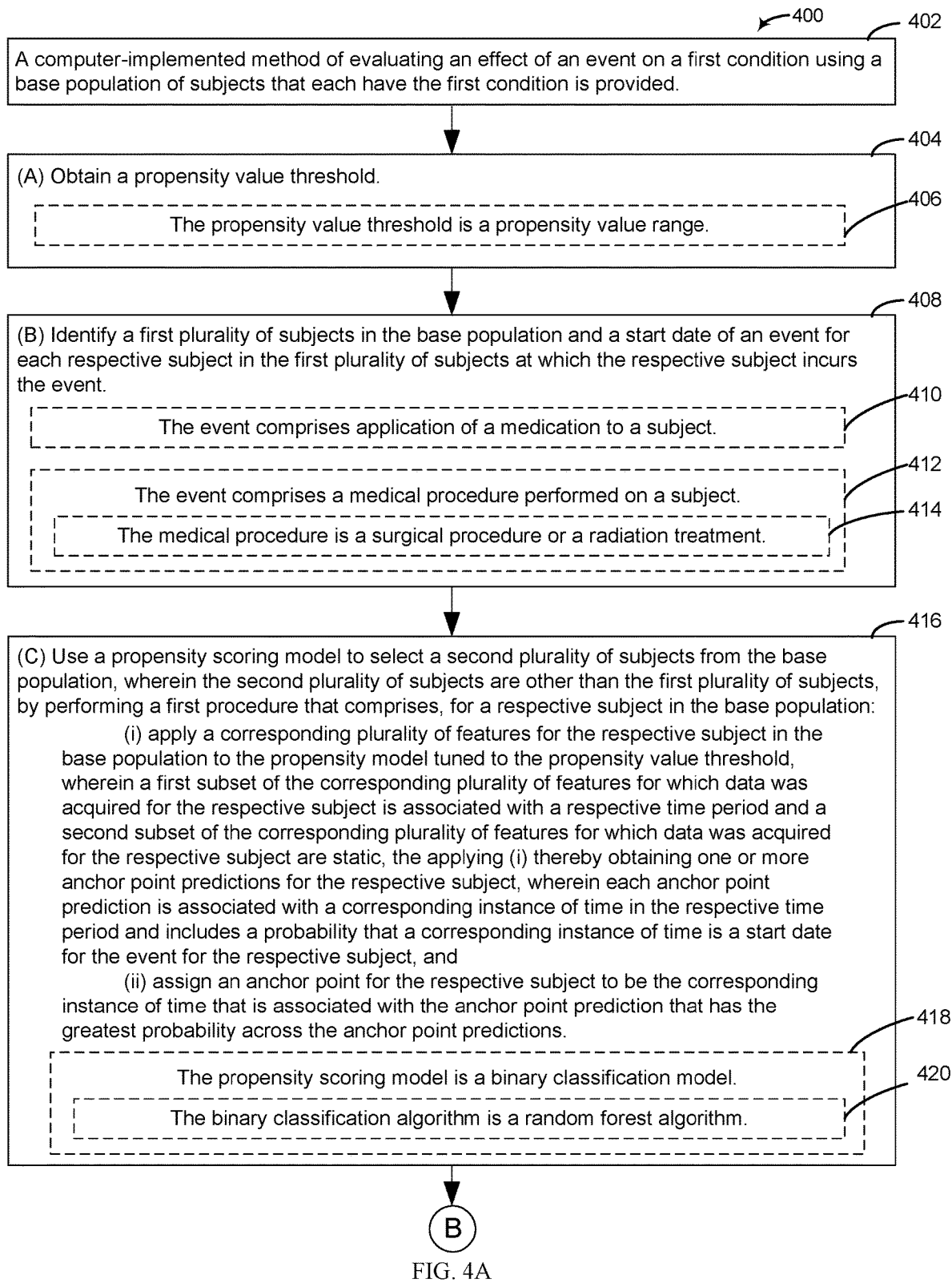
FIGS. 4A and 4B collectively provide a flow chart of processes and features for evaluating an effect of an event on a condition, in which optional blocks are indicated with dashed boxes, in accordance with some embodiments of the present disclosure.
Figure 4B:
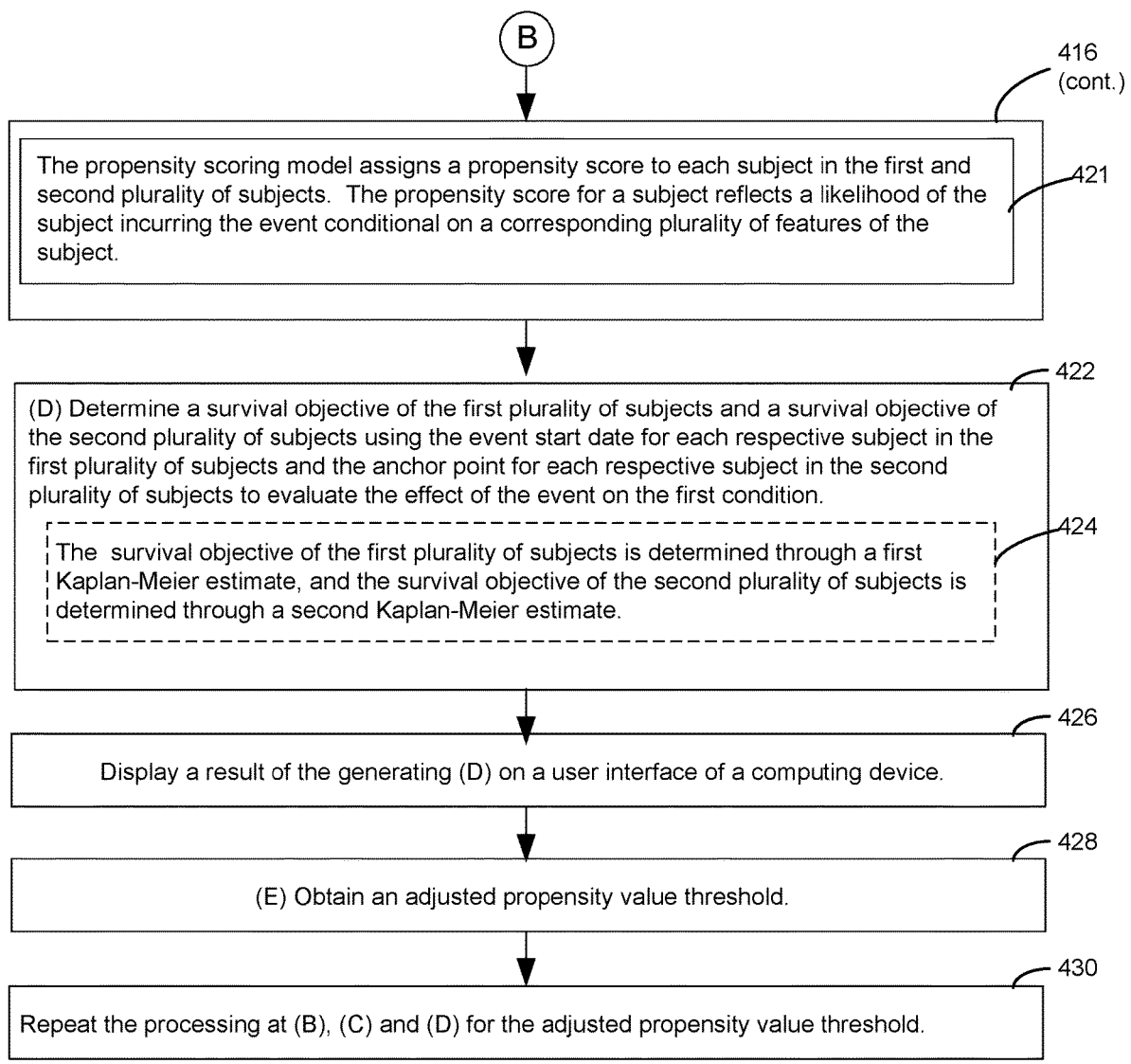

FIGS. 4A and 4B illustrate a computer-implemented method 400 of evaluating an effect of an event on a first condition using a base population of subjects that each have the first condition, as shown at block 402 of FIG. 4A. The first condition can be breast cancer, colon cancer, lung cancer, ovary cancer, prostate cancer, or any other type of cancer. The method involves obtaining a propensity value threshold, at block 404, wherein the propensity value threshold can be, in some embodiments, a propensity value range (block 406).

At block 408, the method 400 includes identifying a first plurality of subjects in the base population and a start date of an event for each respective subject in the first plurality of subjects at which the respective subject incurs the event. The event can be any type of an event. For example, as shown at block 410, the event may comprise application of a medication to a subject. The event can also be a medical procedure performed on a subject (block 412), and the medical procedure can be, for example, a surgical procedure or a radiation treatment (block 414).

At block 416, the method 400 includes using a propensity scoring model to select a second plurality of subjects from the base population, wherein the second plurality of subjects are other than the first plurality of subjects. The using of the propensity scoring model comprises performing a first procedure that comprises, for a respective subject in the base population: (i) applying a corresponding plurality of features for the respective subject in the base population to the propensity model tuned to the propensity value threshold, wherein a first subset of the corresponding plurality of features for which data was acquired for the respective subject is associated with a respective time period and a second subset of the corresponding plurality of features for which data was acquired for the respective subject are static, the applying (i) thereby obtaining one or more anchor point predictions for the respective subject, wherein each anchor point prediction is associated with a corresponding instance of time in the respective time period and includes a probability that a corresponding instance of time is a start date for the event for the respective subject. The using of the propensity scoring model also comprises assigning an anchor point for the respective subject to be the corresponding instance of time that is associated with the anchor point prediction that has the greatest probability across the anchor point predictions. The respective time period can be a period of days, months or years.

In some embodiments, for a respective subject in the second plurality of subjects, the one or more anchor predictions for the respective subject is a plurality of anchor point predictions, a first feature in the first subset of the corresponding plurality of features is measured a plurality of times across the respective time period, and each measurement instance of the first feature is used in a different propensity model calculation to derive a different anchor point in the plurality of anchor points.

In some embodiments, using the propensity scoring model to select a second plurality of subjects is performed for each subject in the base population that is not in the first plurality of subjects.

In some embodiments, the propensity scoring model can be a binary classification model (block 418), which can be, in some embodiments, a model implementing a random forest algorithm (block 420).

In some embodiments, as shown at block 421 of FIG. 4B, the propensity scoring model assigns a propensity score to each subject in the first and second plurality of subjects. A propensity score for a subject reflects a likelihood of the subject incurring an event, conditional on a corresponding plurality of features of the subject. In some embodiments, the propensity scoring model assigns propensity scores to subjects, conditional upon the subjects' features, while ignoring whether or not a particular subject received a treatment. And, in some embodiments, once the propensity score is determined, the subject is assigned to either a treatment or a control cohort based on whether or not a particular subject received a treatment. In some embodiments, a subject is assigned to the treatment or control group based on 1) whether or not the subject receives the treatment in the near future (which can be known prior to receiving a propensity score), and 2) whether or not the subject meets a user-defined propensity threshold range.

Additional examples of the use of propensity scoring that may be used in the present disclosure includes, but is not limited to matching on the propensity score, stratification on the propensity score, inverse probability of treatment weighting using the propensity score, and covariate adjustment using the propensity score. See, for example, Austin, 2011, "An Introduction to Propensity Score Methods for Reducing Effects of Confounding in Observational Studies, Multivariate Behavioral Research 46: 399-424, which is hereby incorporated by reference in its entirety.

In some embodiments, the method comprises identifying the first plurality of subjects and the second plurality of subjects based on a propensity score assigned to each subject, and based on the obtained propensity value threshold, such that each subject is assigned a corresponding propensity score that matches the propensity value threshold.

Accordingly, in some embodiments, the propensity scoring model is tuned to the propensity value threshold such that only those subjects are selected for inclusion in the first plurality of subjects (the treatment cohort) and the second plurality of subjects (the control cohort) that have respective propensity scores that satisfy the propensity value threshold. For example, in embodiments in which the propensity value threshold is a range of values (e.g., [0, 1]), if a subject is assigned a propensity score that is within the selected range for the propensity value threshold, the subject will be deemed to "satisfy" the propensity value threshold and will be included in one of the treatment and control cohorts.

In some embodiments, using the propensity scoring model to identify a first plurality of subjects and a second plurality of subjects is performed on the entire base population.

Various features can be employed in the propensity scoring model. For example, features for a respective subject can comprise a corresponding plurality of demographic features (e.g., age or age group, gender, race, etc.), a plurality of clinical temporal data, and a corresponding plurality of genomic features for the respective subject. The clinical temporal data can include medications taken pre- and post-treatment, censorship rate, stage of a disease (e.g., cancer), etc.

In some embodiments, non-limiting examples of features in the second subset of features includes gender, race, or year of birth, family history, body weight, size, or body mass index.

In some embodiments, a feature in the first subset of features is months since birth, smoking status, menopausal status, time since menopause, time since last smoked, primary cancer site observed, metastasis site observed, cancer recurrence site observed, tumor characterization, medical procedure performed, medication type administered, radiotherapy treatment administered, time since primary diagnosis, time since predefined cancer stage diagnosed, time since metastasis, time since last recurrence of cancer, time since medical procedure performed, time since predefined medication taken, time since radiotherapy treatment administered, imaging procedure performed, change in tumor characteristic, rate of change in tumor characteristic, or predetermined response observed.

In some embodiments, a first feature in the plurality of features is obtained from a biological sample of the respective subject and corresponds to a DNA for a predetermined human gene.

In some embodiments, the first feature is a count of germline mutations observed for the DNA in the biological sample of the respective subject. In some embodiments, the first feature is a count of somatic mutations observed for the DNA in the biological sample of the respective subject.

In some embodiments, a first feature in the plurality of features is a number of somatic mutations on a predetermined chromosome as determined by sequencing RNA from a biological sample obtained from the respective subject. In some embodiments, a first feature in the plurality of features is a number of germline mutations on a predetermined chromosome as determined by sequencing DNA from a biological sample obtained from the respective subject.

In some embodiments, a first feature in the plurality of features is a number of genes with mutations on a predetermined chromosome as determined by sequencing DNA from a biological sample obtained from the respective subject.

In some embodiments, a first feature in the plurality of features is a mutation density of a predetermined chromosome as determined by sequencing DNA from a biological sample obtained from the respective subject.

In some embodiments, a first feature in the plurality of features is a number of mutations of a defined mutational class of a predetermined chromosome as determined by sequencing DNA from a biological sample obtained from the respective subject. The defined mutational class can be single nucleotide polymorphism (SNP), multiple nucleotide polymorphism (MNP), insertions (INS), deletion (DEL), or translocation.

In some embodiments, each feature can be categorized into a "feature class," which can be "static" (features a subject that do not change over time) or "temporal" (features of a subject that are associated with a specific time point and that can change over time). In addition to being assigned to a feature class, each feature can also be assigned to a "temporal class" such as (i) "past"—a historic value of the feature or event, the fact that it has taken place in the past, or the time since it took place, (ii) "present"—a current value of the feature or event at the specified time point; or (iii) "future"—a future value of the feature or event, the fact that it will take place in the future, or the time until it takes place in the future. It should be noted that "future" features may be used for interactive exploration of the cohorts via the user interface rather than for training of the propensity model.

As an example, gender, face, and year of birth can be categorized as features of a "static" feature class and of a "past" temporal class. The features such as months since birth, smoking status, menopausal status, comorbidity observed, months since menopause, months since last smoked, months since comorbidity observed, primary cancer site observed, metastasis site observed, cancer recurrence site observed, tumor characterization, procedure performed, a type of a medication administered, a type of a radiotherapy administered, months since primary diagnosis, months since a diagnosis of a certain stage of a condition, months since the first or last occurrence of a certain event, months since a procedure was administered, months since a medication was administered, months since a radiotherapy was administered, imaging procedure performed (and results of the procedure—e.g., a determined tumor size and other tumor characteristics), change in a tumor characteristic, rate of change in a tumor characteristic, an observed response, a number of certain events observed per a time period can be categorized as "temporal" features that belong on all three ("past," "present" and "future") temporal classes.

In some embodiments, the use of the propensity scoring model to identify propensity matched treatment and control cohorts allows estimation of survival curves in the treatment and control cohorts. At block 422 of FIG. 4B, the method 400 further includes determining a survival objective of the first plurality of subjects and a survival objective of the second plurality of subjects using the event start date for each respective subject in the first plurality of subjects and the anchor point for each respective subject in the second plurality of subjects to evaluate the effect of the event on the first condition. In some embodiments, as shown at block 424, the survival objective of the first plurality of subjects is determined through a first Kaplan-Meier estimate and the survival objective of the second plurality of subjects is determined through a second Kaplan-Meier estimate.

In some embodiments, determining the survival objective of the first plurality of subjects and the survival objective of the second plurality of subjects is performed using a survival model applied to the treatment and control groups. The survival model may be trained using an algorithm with the survival objective as an objective response variable. The survival objective may be time until death, time until progression of the first condition, or time until an adverse event associated with the first condition is incurred. The survival model can be constructed and trained using various features, including the features that are used for the propensity scoring model. It should be noted that the survival objective modeling is performed separately from propensity modeling. Information on patients is assessed and filtered based on prior survival (progression-free survival (PFS)/overall survival (OS)) likelihoods.

In some embodiments, a survival modeling approach is based on a temporal modeling of patient survival, which can be, for example, a regression based prediction of expected survival from a point in time or classifier for probability of surviving more than X years from a point in time. The inception point of the model prediction (i.e., what the "point in time" actually is) can vary. For example, it can be survival from a first diagnosis of primary cancer, survival from prescription of a specific medication or procedure, survival from a specific stage diagnosis, etc. The survival objective can also vary depending on a model. For example, the approach can involve modeling a time until death, a time until progression, a time until adverse event, etc.

Referring back to FIG. 4B, the result of the determining the survival objective of the first plurality of subjects and the survival objective of the second plurality of subjects can be displayed on a user interface of a computing device, as shown at block 426.

In some embodiments, the method further comprises displaying on a user interface a respective average value for each feature in one or more features in the plurality of features in the first plurality of subjects and a respective average value for each feature in one or more features in the plurality of features in the second plurality of subjects. For example, features (sub)panel 318 (FIG. 3) can be used to display, for each of the treatment and control groups, various features and their corresponding average values, though the feature values can be presented in any other ways. For example, a percentage of the subjects in the group associated with a certain feature can be presented. Non-limiting examples of the features include clinical data, age group, race, stage of cancer, gender, drugs taken pre- and post-treatment, censorship rates, etc. It should be noted that some or all of these features may be different from the features used to build and train the propensity scoring model. The features can be presented automatically and/or in response to user input.

As discussed above, the propensity value threshold can be adjustable, for example, via a user interface through which user input can be received to select a value or a range of a propensity value threshold. Thus, an adjusted propensity value threshold can be obtained (block 428), which can be done, for example, via a user interface. For example, user input can be received via the user interface element 308 of FIG. 3 such that a certain range of a propensity value threshold is selected (e.g., a different range from a previously selected range). As discussed above, the propensity value threshold is used to determine which subjects from the identified treatment and control cohorts to select as a result of the application of a propensity scoring model. In some embodiments, the treatment and control cohorts are identified in the base population of subjects such that the respective subjects have a similar propensity score or value, and the propensity value threshold, such as a range, is used to select the subjects from the treatment and control cohorts that have a propensity score within the range. The propensity value threshold may determine subjects to select for the treatment and control cohorts by limiting selection to those subjects having anchor points with a respective probability satisfying the propensity value threshold. A probability may satisfy the threshold, depending on the mode of operation, by falling below a lower threshold, exceeding an upper threshold, or falling below an upper threshold and exceeding a lower threshold.

Once the adjusted propensity value threshold is obtained at block 428, the identifying a first plurality of subjects (block 408), the using a propensity scoring model (block 416), and the determining a survival objective of the first plurality of subjects and a survival objective of the second plurality of subjects (block 422) can be repeated for the adjusted propensity value threshold, as shown at block 430 of FIG. 4B. In this way, different treatment and control groups can be selected, and related information, including survival analytics information (e.g., survival curves) can be presented on the user interface. It should be noted that the selection of different treatment and control groups for presentation and analysis, upon the adjustment of the propensity value threshold, involves selection of different subjects from the treatment and control groups previously identified using the propensity scoring model.

Examples

In some embodiments, a propensity scoring model may be used to predict a likelihood of a subject from a base population of subjects receiving a treatment X (e.g., a specific drug, radiotherapy, or procedure), for the first time, in the next T interval (e.g., 16 to 25 days). In some embodiments, a cross-validation using 8×2 stratified folds can be used. Features from a feature dataset, including demographic, genomic, and clinical temporal data, defined historically at each time point of a subject's timeline, are used. An 8×2 patient-based, key attribute stratified, cross-validation fold split is utilized for evaluation. Once the predictions of the likelihood of a subject's receiving a treatment X are available, the method in accordance with the present disclosure identifies a treatment group (the subjects who were administered the treatment) and a control group (the subjects who were not administered the treatment). An anchor point is determined for each patient in the control group as the highest likelihood point of the treatment being administered. The anchor point is used to determine the starting point for the control survival curve.

In some embodiments, the propensity scoring model is implemented as a binary classification model. In some embodiments, the binary classification model is trained to maximize a receiver operating characteristic (ROC)/area under the curve (AUC) metric. The propensity scoring model may be trained using a random forest algorithm with a multi-label objective, on a per cancer+treatment class basis (e.g., a propensity scoring model for lung cancer medications, a propensity scoring model for lung cancer procedures, etc.), with separate objective response variables for each of the available treatments of that treatment class (which can be tens to hundreds). Non-limiting examples of treatments include radiotherapy, chemotherapy, various surgical procedures, implant placement, and various medications. Other algorithms, including machine learning algorithms, a gradient boosting algorithm, linear or logistic regression, or a neural network may be applied as the propensity scoring model. Out-of-fold predictions can be made and stored for future use.

FIGS. 5A 5B, 5C and 5D illustrate an example of an embodiment of a user interface 500 of a tool such as, e.g., user interface 307 shown in FIG. 3. The tool user interface 500 can be implemented as an interactive dashboard supported by the propensity score model. The tool, which can be implemented as part of another tool allowing development and assessment of clinical trials, can be initiated in a suitable manner. For example, in some embodiments, the described techniques may operate in conjunction with a system for predicting and analyzing patient cohort response, progression, and survival, as described, for example, in U.S. Provisional Patent Application No. 62/786,739 filed Dec. 31, 2018, which is incorporated by reference herein in its entirety.

Figure 5A:
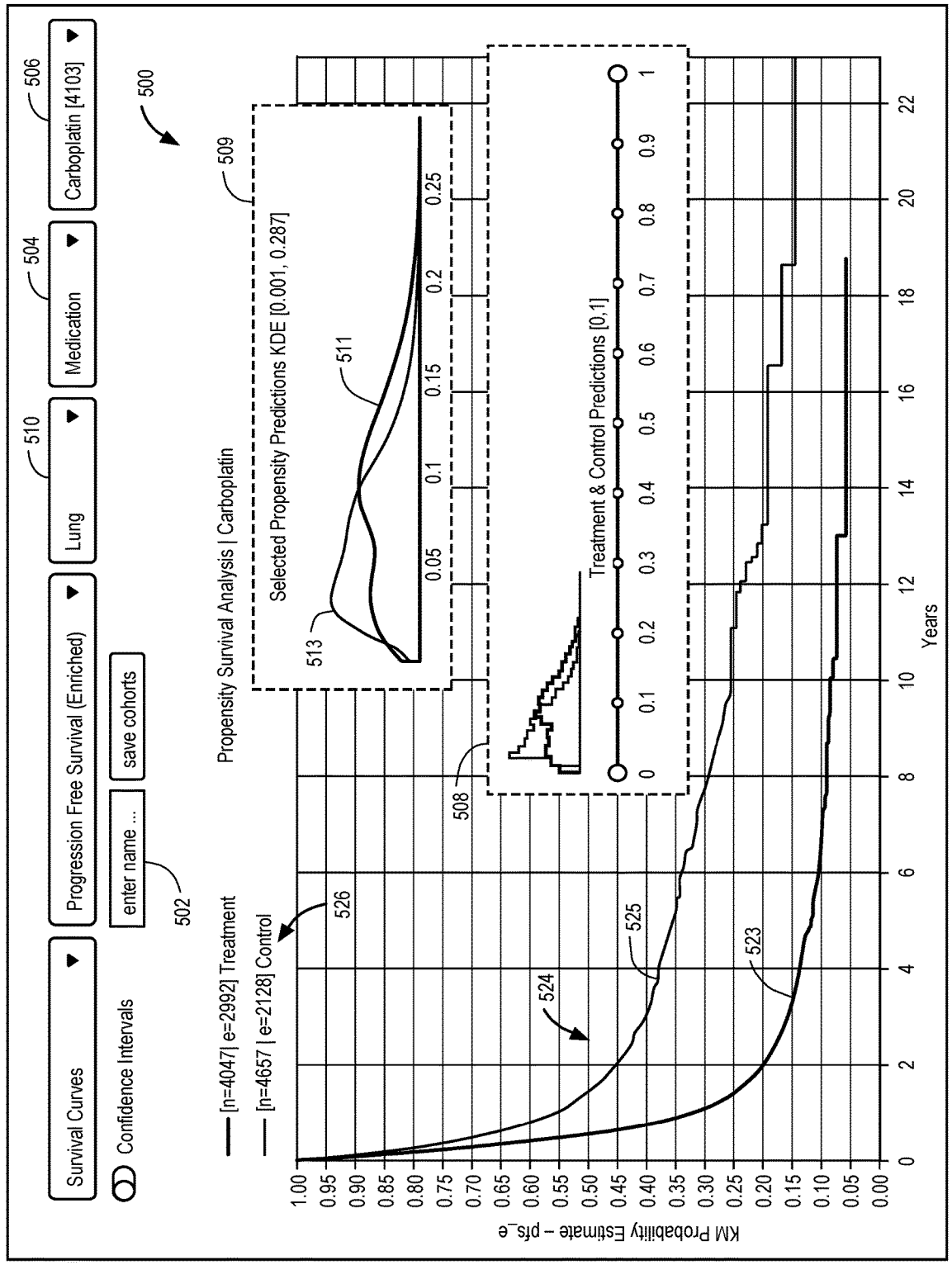

As shown in FIG. 5A, a user interface element 502 can be used to receive user input indicating a selection of a base population of subjects which is, in this example, a base population of subjects having cancer. A lung cancer can be selected based on respective user input, via a user interface element 510. It will be appreciated that user interface element 510 provides any number of disease states or other forms of states that can be selected. A type of a treatment (medication) and the specific medication (carboplatin) can be selected via a user interface elements 504 and 506, respectively. A user interface element 508 can be used to obtain a propensity value threshold, which is a range between 0 and 1 in the illustrated embodiment. No selection is shown in this example such that the entire range is chosen. Other selections made via the user interface 500 include survival curves as a survival objective representation and progression free survival as a survival objective.

In response to obtaining the selection of the parameters via the user interface 500, treatment and control cohorts are identified in the base population of the subjects such that the treatment cohort includes 4047 subjects and the control cohort includes 4657 subjects, as shown in FIG. 5A (526). The survival curves 524 are generated for the treatment and control cohorts and displayed in a propensity survival analysis portion of the user interface 500. The survival curves 524, comprising a survival curve 523 for the treatment cohort and a survival curve 525 for the control cohort, are generated as Kaplan-Meier estimates ("KM Probability Estimates") versus years. As also shown in FIG. 5A, kernel density estimation (KDE) plots 509 ("Selected Propensity Predictions KDE") are generated and displayed, which allow assessing an overlap between the matched treatment (a plot 511, shown in purple) and control (a plot 513, shown in grey) cohorts. Different average respective starting time points for the control and treatment cohorts may be selected, depending on a propensity value threshold selection, feature selection, and, in some embodiments, additionally on a change in a likelihood to progress threshold.

Figure 5B:
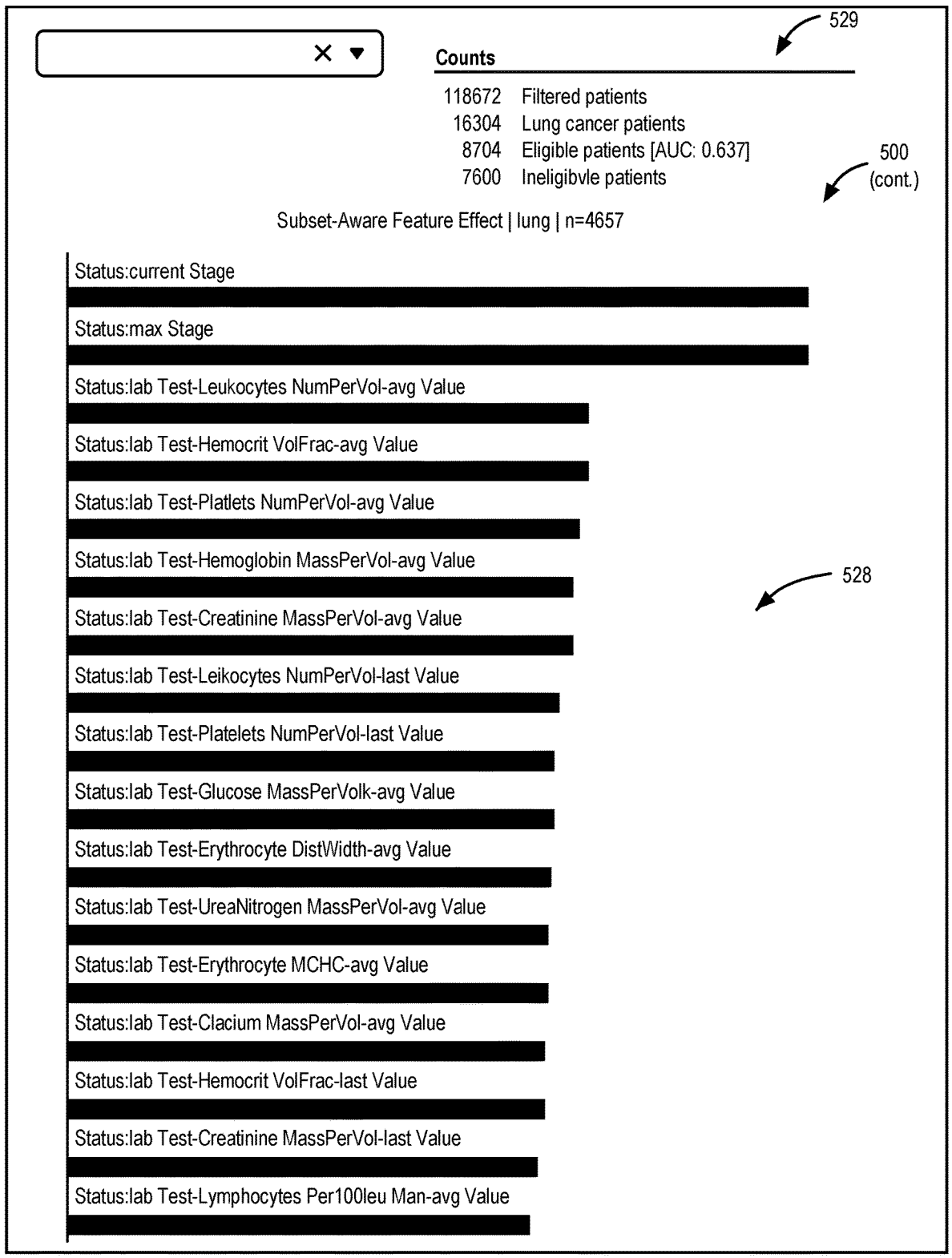

As discussed above, embodiments of the present disclosure allow assessing features of the subjects in the treatment and control groups that were used in the propensity scoring model applied to the base population to identify the matched cohorts. Thus, a panel 528 ("Subset-Aware Feature Effect") in FIG. 5B presents the features that contributed the most to the predictions made by the utilized propensity scoring model. In this example, the most significant features (shown as the top bars) are a current stage and a maximum stage of lung cancer. Other features include an average value (a number per volume) of leukocytes, an average value (volume/fraction) of hematocrit, an average value (a number per volume) of platelets, an average value (mass per volume) of hemoglobin, an average value (mass per volume) of creatinine, a last value (a number per volume) of leukocytes, a last value (a number per volume) of platelets, an average value (a number per volume) of glucose, etc. In addition, FIG. 5B shows, in a panel 529, counts of subjects in the base population, including a total number of subjects (118672), a number of lung cancer patients (16304) (that would be taken as a base population of subjects), a number of patients eligible for inclusion in the described analysis (8704), and a number of ineligible patients (7600).

In FIG. 5B, features shown in panel 528 are ranked in accordance with their importance in differentiating the base population of the patients into the treatment and control cohorts. In this example, the information on the features is visualized in the form of bars, though it should be appreciated that any other visual representation can be used to indicate which features effected the selection, by the model, of the treatment and control cohorts. The length of the bar may correspond to the number of patients in the cohort which presented the feature and were predicted to have metastasized or did not metastasized. For example, each feature may be hierarchically organized by rows into the ranking of the features by importance to the predictions. A first color may identify features which are most important for predicting metastasized and a second color may identify features which are most important for predicting did not metastasize. A first row may identify the first feature and may represent the greatest determining factor in the prediction of metastasized and did not metastasize and may be 'cancer stage 3 or greater.' The feature may, based upon the results of the adaptive algorithm, have the bar with the greatest length to visually represent the feature's importance and the first color to indicate that the feature weighs most toward metastasized. A second row may identify the second feature and may represent the greatest determining factor in the prediction of metastasized and did not metastasize and may be 'took_medication: heparin.' The feature may, based upon the results of the adaptive algorithm, have the bar with the second greatest length to visually represent the feature's importance and the second color to indicate that the feature weighs most toward did not metastasize. Features continuing down the list may have increasingly shorter bars of either the first or second color to indicate their respective weights for or against the predictions for metastasis.

Figure 5C:
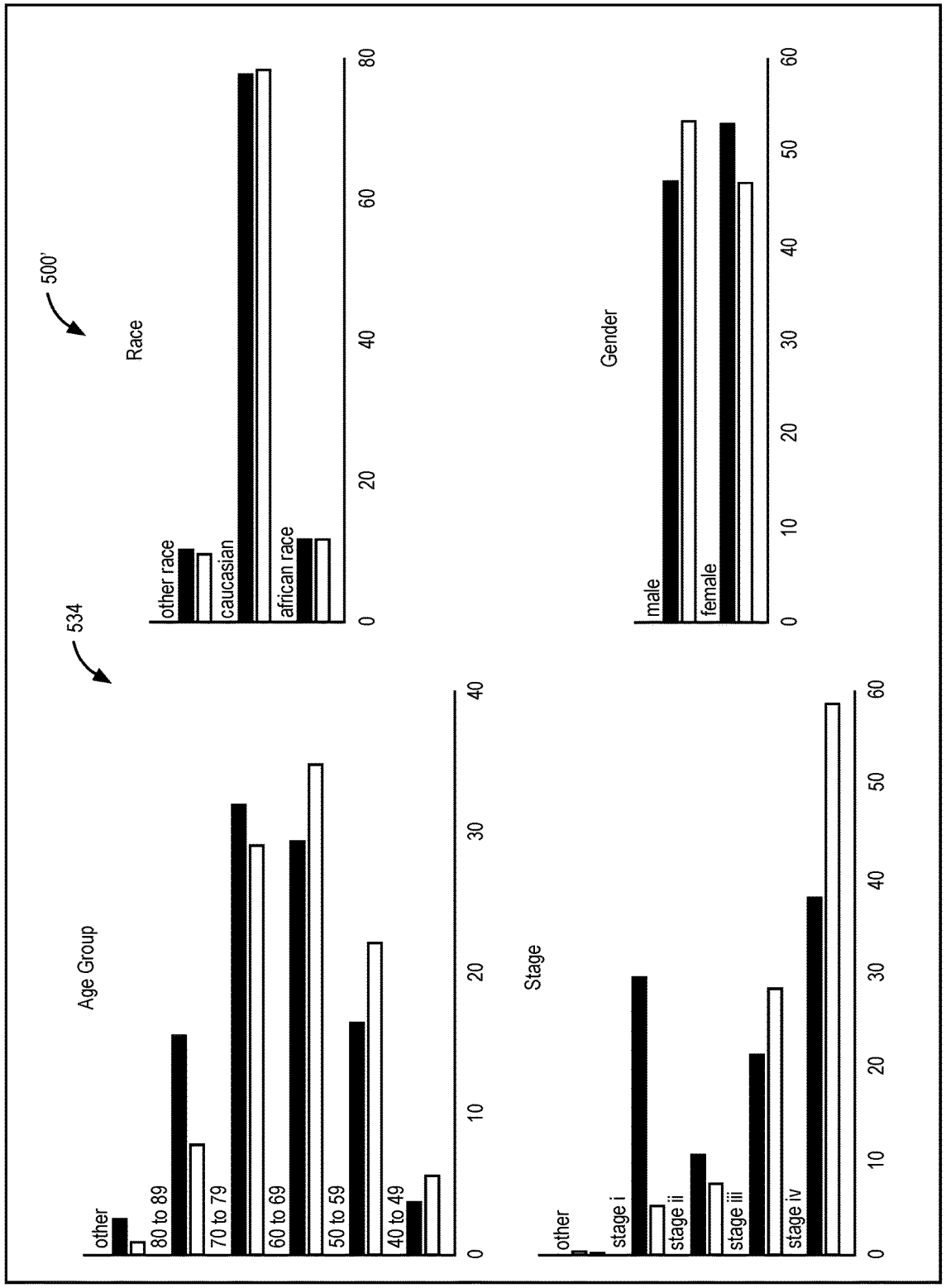

FIGS. 5C and 5D collectively illustrate another portion 500' of the tool's user interface 500 (which can be presented concurrently with the elements shown in FIGS. 5A and 5B) that illustrates, in a panel 534, features among the control cohort (grey bars shown above the purple bars for each pair of bars) and the treatment cohort (the purple bars). The displayed features are age group, race, stage of a lung cancer (other, stage I, stage II, stage III, and stage IV), and gender (male, female). The portion 500' of the tool's user interface 500 also displays information on features (types of the features and corresponding values) of the subjects in the control group (530) and in the treatment group (532). As shown in FIG. 5D, the panels 530 and 532 display a censorship rate, distinct medications taken, and drugs taken pre- and post-administration (or predicted administration) of the studied treatment (carboplatin, in this example).

Figure 6A:
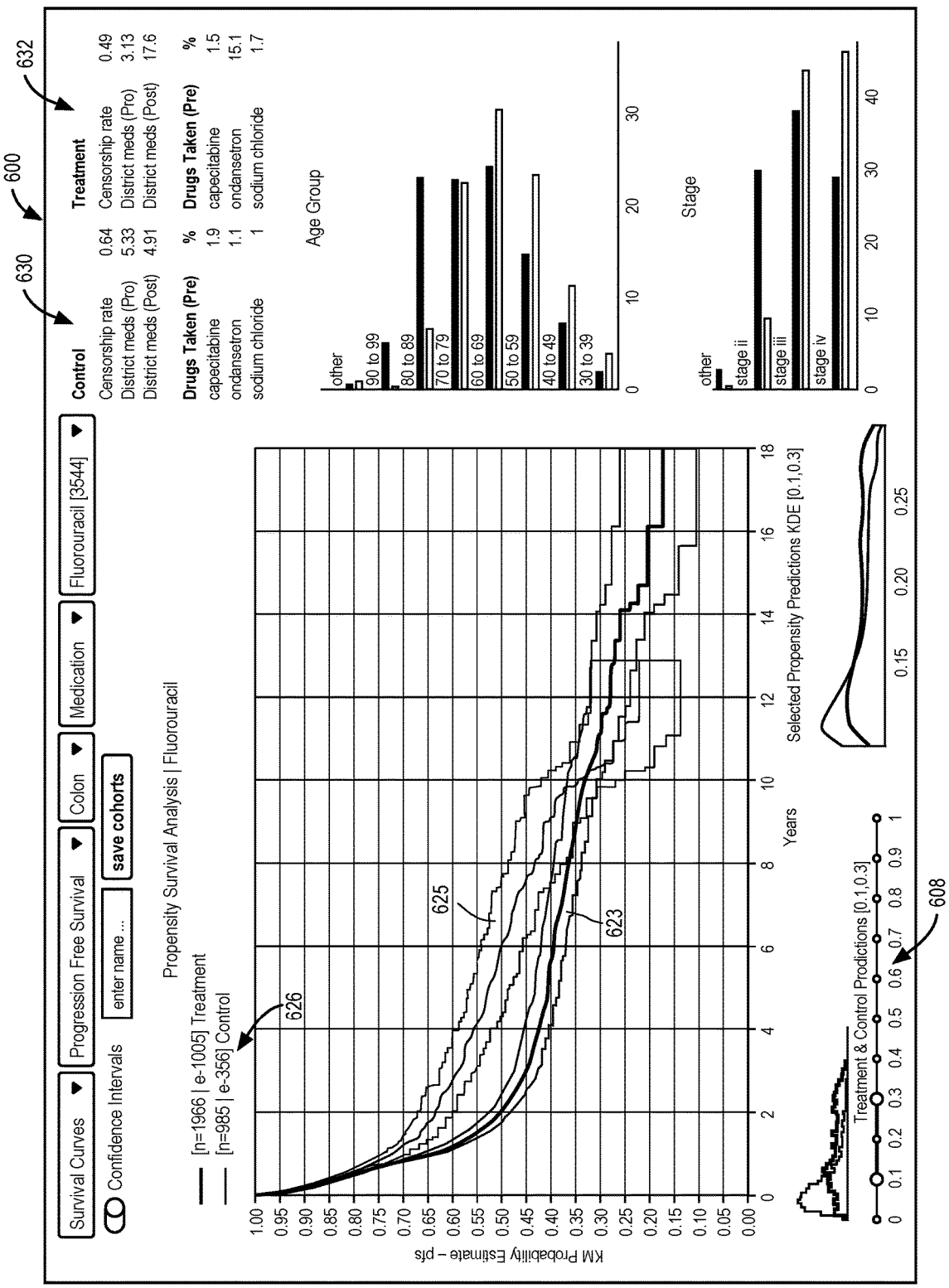
Figure 6B:
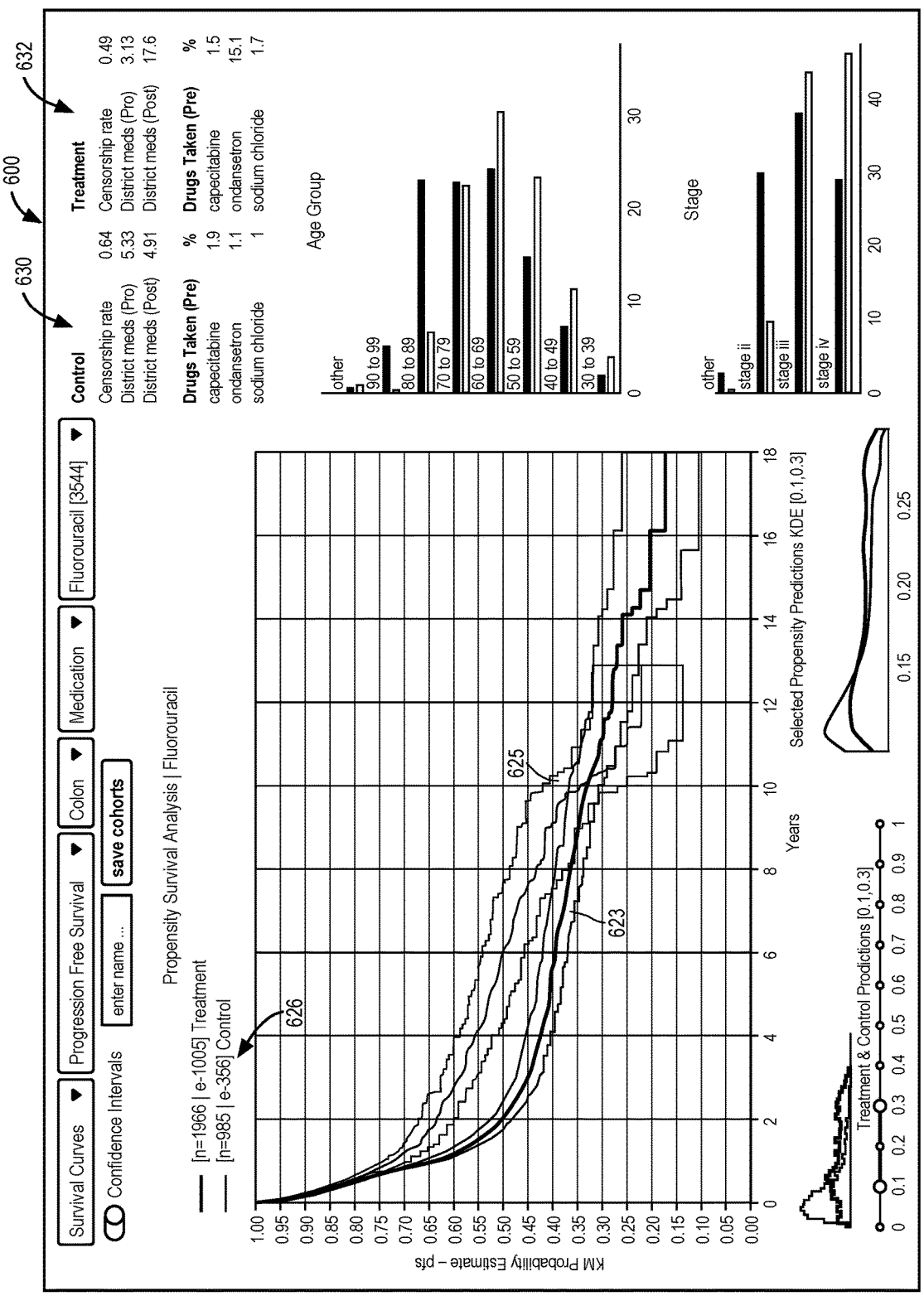

FIGS. 6A, 6B, and 6C illustrate another example of an embodiment of a tool user interface 600 in accordance with the present disclosure. As shown in FIG. 6A, a propensity value threshold 608 acquired via the user interface 600 in a range of between 0.1 and 0.3. In this example, the condition is a colon cancer and the medication is fluorouracil. The type of the information presented on the user interface 600, generated using a propensity scoring model in accordance with embodiments of the present disclosure, is similar to the information shown in user interface 500 (FIGS. 5A and 5B). In FIGS. 6A and 6B, 1966 subjects are assigned to a treatment group (a survival curve 623), and 985 subjects are assigned to a control group (a survival curve 625), as shown in a location 626 on the user interface 600.

FIG. 6B shows data identical to that in FIG. 6A but with additional notations that facilitate interpretation of the results. As indicated on FIG. 6B, from evaluating the survival curves 623, 625 for the treatment and control groups, the treatment group ("arm") appears to have a worse performance in terms of survival as compared to the control group. Evaluation of features of the control group (panel 630) and features of the treatment group (panel 632), including drugs taken pre-treatment (the percentage across the respective group is shown for each drug) demonstrates that the subjects in the treatment group were already taken an anti-nausea medication (ondansetron) which can affect the results of the evaluation of the effect of fluorouracil on colon cancer. FIG. 6B also emphasizes that the control group included older subjects even after the application of the propensity scoring model ("score matching") that aims at ensuring that the subjects in the treatment and control groups have similar demographic, clinical, and other characteristics. Also, the subjects in the treatment group had (on average) a higher stage of the colon cancer than the subjects in the control group. Accordingly, the seemingly worse survival of the subjects in the treatment group can potentially explained by the fact that these subjects had a more advanced stage of the disease than the matched control group. FIG. 6C illustrates a close-up, with some notations, of the panels 630 and 632 presenting features of the control and treatment groups, respectively.

Figure 7:
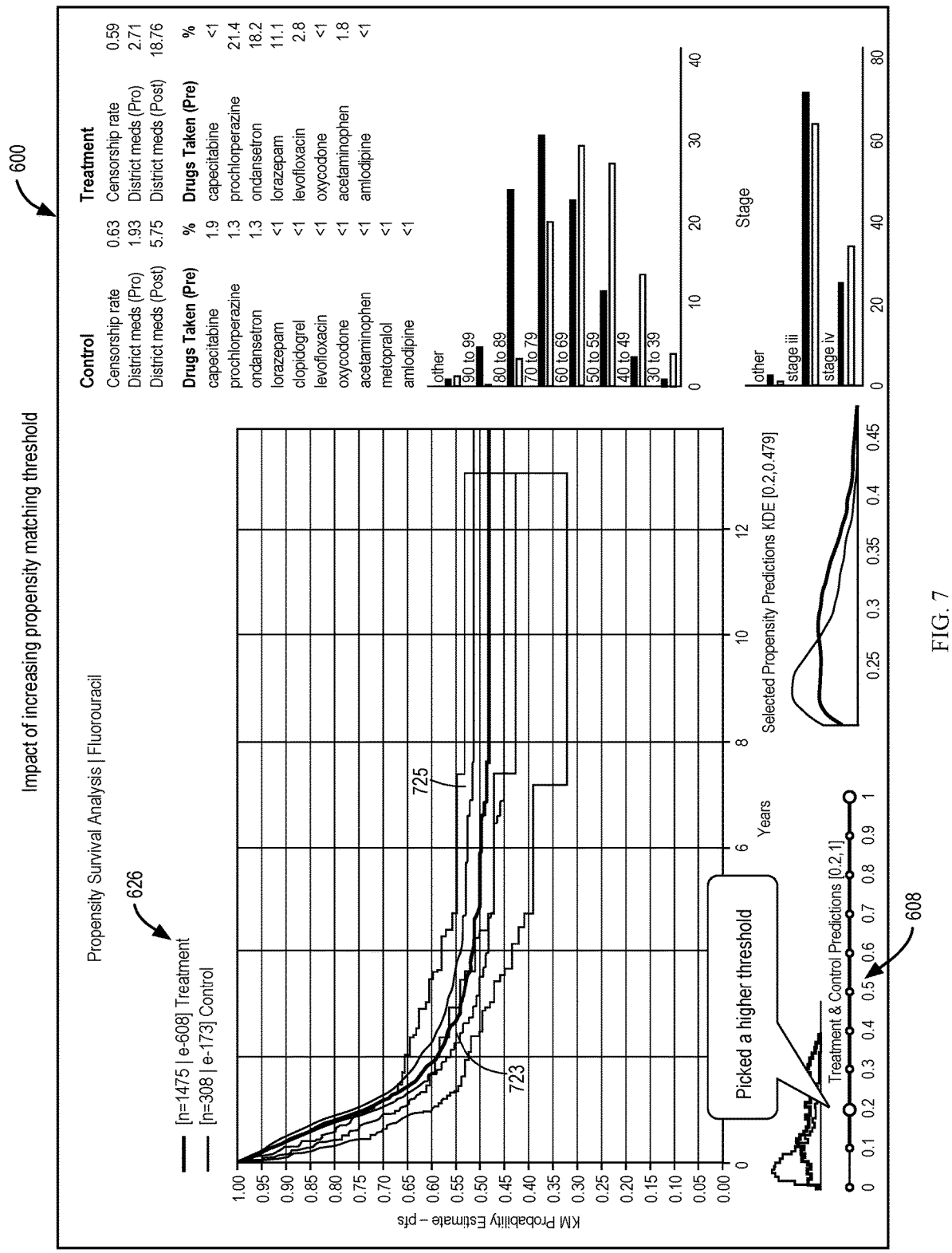
FIG. 7 is a diagram illustrating the user interface of FIGS. 6A-6C where a higher propensity value threshold is obtained, in accordance with some embodiments of the present disclosure.

FIG. 7 illustrates an example of an embodiment of the tool user interface 600 in accordance with embodiments of the present disclosure, demonstrating impact of increasing a propensity value threshold (referred to as a "propensity matching threshold") in the example of FIGS. 6A-6C. The same base population of subjects as used in the example of FIGS. 6A-6C is analyzed. As compared to FIGS. 6A-6C, a higher propensity value threshold (i.e., a range between 0.2 and 1) is acquired in this example via the user interface element 608. For example, the user interface element 608 can be implemented as a slider element configured to receive user input indicating a selection of a range of values.

Adjusting a propensity value threshold results in different treatment and control groups selected from the base population of subjects, with the higher value for the propensity value threshold leading to a more stringent selection of subjects for the two matched groups. In other words, the higher the propensity value threshold, the more similar groups are identified by the propensity scoring model (though the similarity depends on the features selected for the model).

In the example illustrated in FIG. 7, the adjusted propensity value threshold (see, e.g., block 208 of FIG. 2) results in treatment and control groups of sizes different than in the example of FIGS. 6A-6C. The adjusted propensity value threshold is used to select certain subjects from the treatment and control groups (where each subject is assigned to one of the groups) for presentation and analysis. Thus, as shown in the location 626 on the user interface 600, the treatment group includes 1476 subjects and the control group includes 308 subjects. A survival curve 723 (shown in purple) for the treatment group and a survival curve 725 (shown in grey) for the control group illustrate a noticeable difference as compared to survival curves 623, 625 for the treatment and control groups, respectively, shown in FIGS. 6A and 6B. In the example of FIG. 7, the control group still has, on average, older subjects that in the treatment group. At the same time, the control and treatment groups are more balanced with respect to the stage of colon cancer, meaning that the subjects in the two groups have a similar distribution of stages of colon cancer.

Figure 8A:
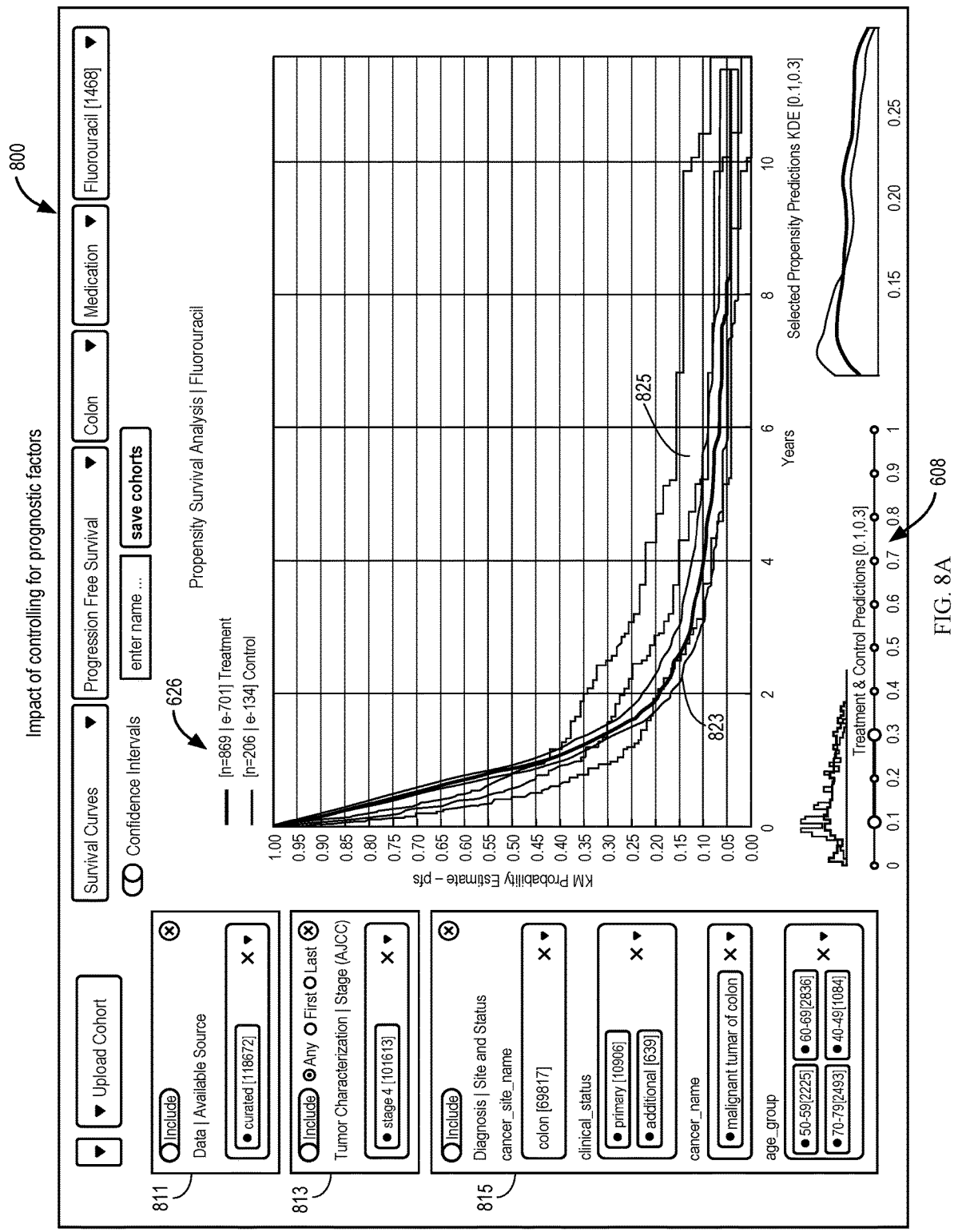
FIGS. 8A and 8B are diagrams collectively illustrating the user interface of FIGS. 6A-6C where features for a propensity scoring model are obtained based on user input, in accordance with some embodiments of the present disclosure.
Figure 8B:
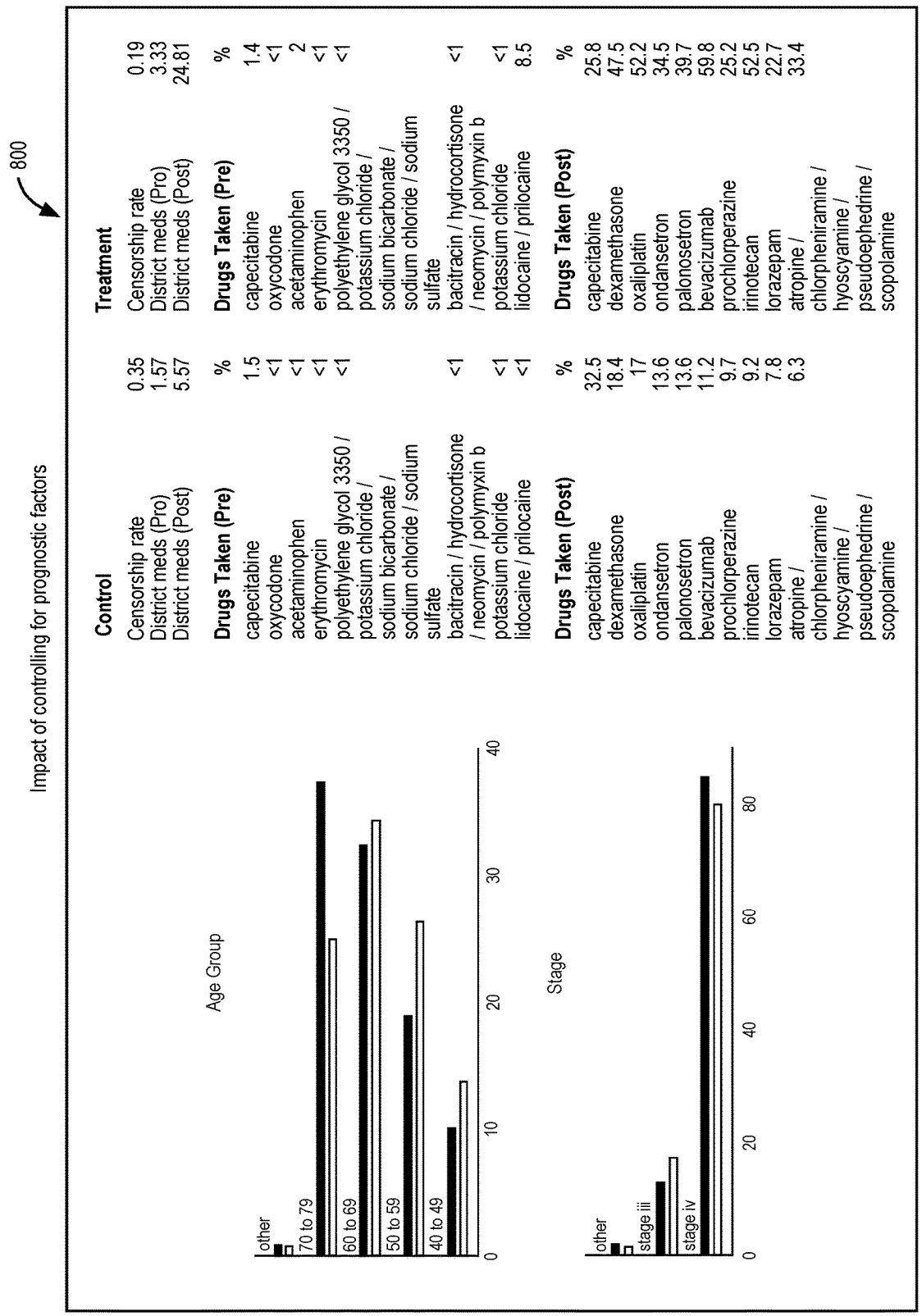

FIGS. 8A and 8B illustrate an example of an embodiment the tool user interface 600 of FIGS. 6A-6C, which is shown as a tool user interface 800 demonstrating impact of acquiring (based on user input, in this example) of a selection of certain features ("controlling for prognostic factors") for propensity survival analytics. The same base population of subjects as used in the example of FIGS. 6A-6C and FIG. 7 is analyzed. The tool user interface 800 is shown to include a feature selection module 810 that is presented in addition to other visual elements, as shown in connection with the user interface 600. It should be noted that the user interface 500 (FIGS. 5A and 5B) and the user interface 600 shown in FIGS. 6A-6C and FIG. 7 can also have a feature selection module. In the present example, the feature selection module 810 can be displayed upon a user selection of a certain element on the user interface, or in response to another trigger. It can also be presented automatically.

As shown in FIG. 8A, the feature selection module 810 has several modules that are configured to receive selection of various features, such as a module 811 ("Data|Available Source") that allows selecting features based on their source (e.g., a curated database, as shown in this example), a module 813 ("Tumor Characterization) Stage (AJCC)") that allows selecting a tumor characterization feature (e.g., a cancer stage, as shown in FIG. 8A), and a module 815 ("Diagnosis|Site and Status") that allows selecting features related to tumor name, site, and status, as well as an age group. It should be appreciated that the modules 811, 812, 815 are shown by way of example only, as any other user interface elements can be included in the feature selection module 810, for receiving selection of any suitable features.

In this example, as shown in FIG. 8A, the selected features include a stage of cancer (stage 4), a cancer type (colon), cancer clinical status (primary and additional statuses), cancer name ("malignant tumor of colon"), and age groups (40-49, 50-59, 60-69, and 70-79). The older (above 40) age group can be selected by the user, for example, based on the results of the analysis as shown in FIG. 6B where it was observed that the control group is generally older. The same propensity value threshold is selected via the user interface element 608 as in FIGS. 6A-6C—in a range of between 0.1 and 0.3. As shown in the location 626 of the user interface 800 in FIG. 8A, the number of subjects in the identified treatment and control groups is reduced to 869 and 206, respectively. This, in combination with the controlling for a cancer stage and age group, results in different survival curves 823 (shown in purple) and 825 (shown in grey) for treatment and control groups, respectively. As noted in FIG. 8A, a large change occurs in a short-time relative placement of the respective survival curves for the treatment and control groups. FIG. 8B illustrates features of the control and treatment groups (with the top (grey) bar representing the control group in each of the control/treatment pairs), and includes notations regarding the analysis of the features, such as a treatment group still being slightly younger than a control group and a better balance between the subjects in the treatment and control groups in terms of cancer stage. Thus, as shown, an improved cancer stage balance between the group is achieved as compared to the stage distribution shown in FIG. 6B (without selecting the age groups).

In some embodiments, a propensity scoring model is used to divide the base population of subjects into treatment and control groups. Also, as mentioned above, in some embodiments, one or more subjects may not be assigned to either of the treatment cohort or the control cohort. A propensity value threshold is then used to select different subjects from the pre-identified treatment and control groups for further survival analysis and other types of analyses. Accordingly, as the propensity value threshold is adjusted, a size of the treatment and control cohorts information on which is presented on a user interface can vary. Other information will vary as well. For example, different event start dates and different anchor points (aligned to each other for generating KM, or other estimates) may be used for survival objective analysis, depending on the value or range of the propensity value threshold. Thus, it should be appreciated that the treatment and control cohorts are pre-identified by the propensity scoring model, and it is the selection of different propensity value thresholds, subjects' features, and, in some embodiments, different survival propensity value thresholds by a user that allows assessing and comparing respective portions of the subjects from the treatment and control cohorts, depending on goals of a clinical trial or other task.

Figure 9A:
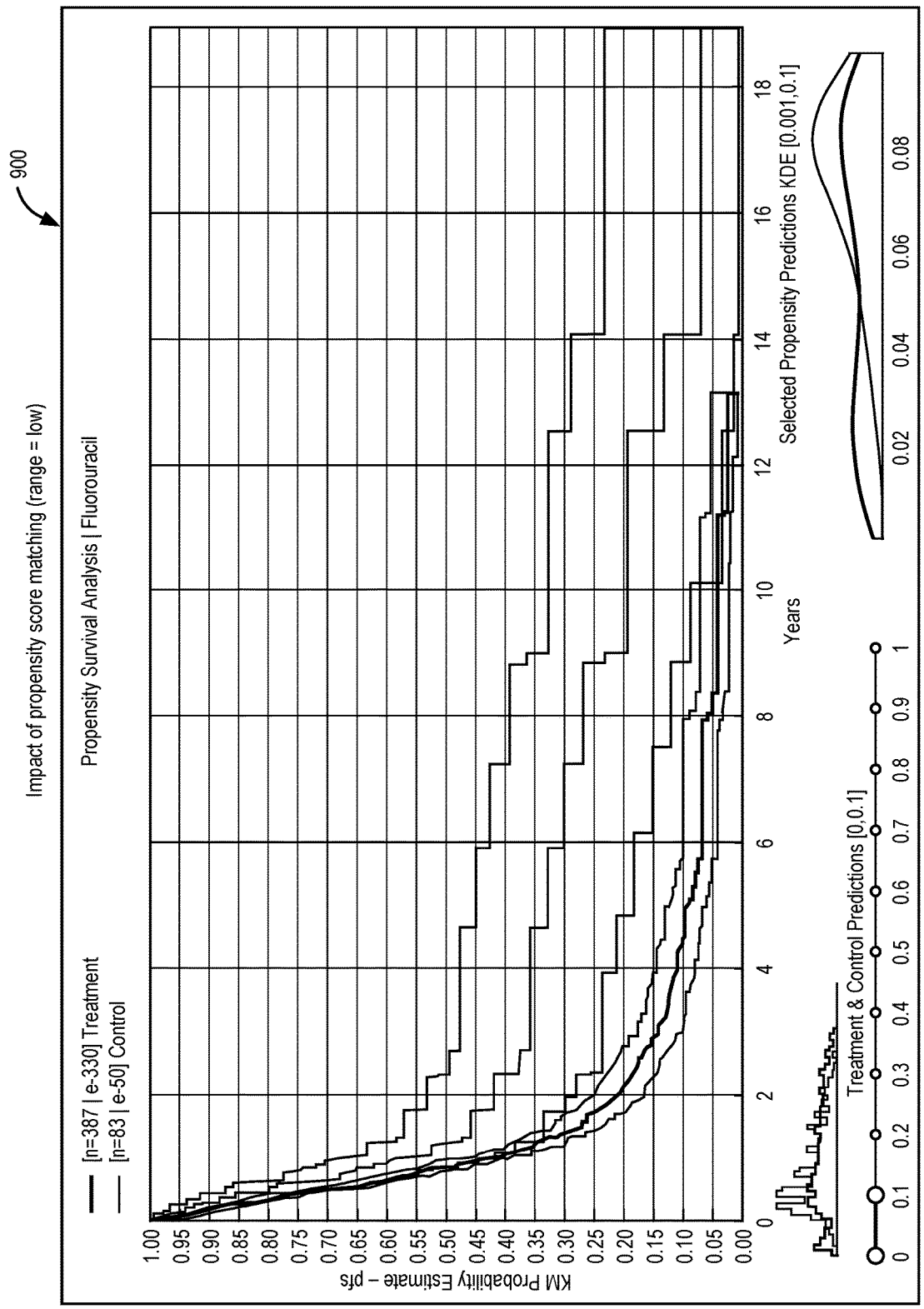
Figure 10A:
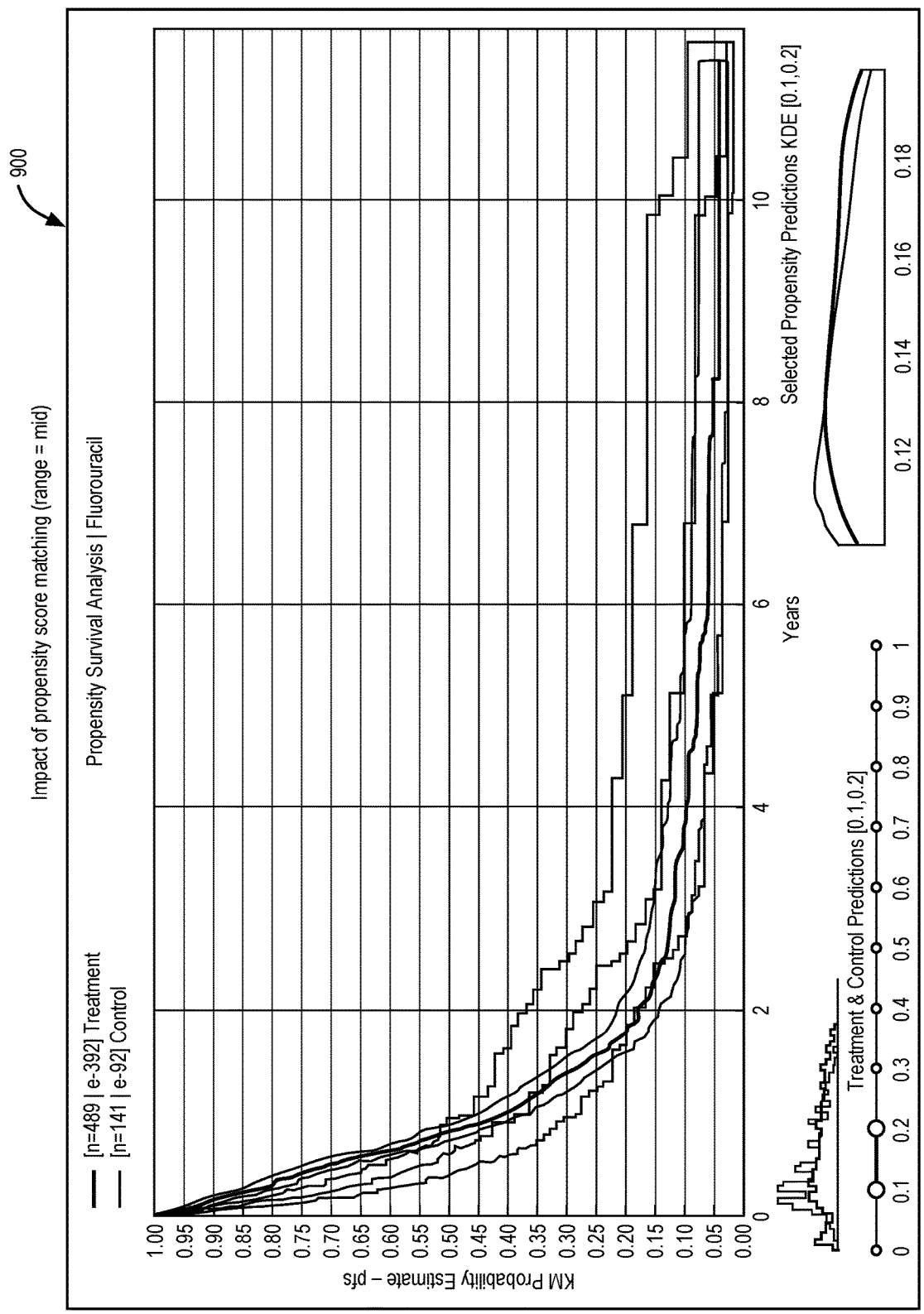
Figure 11A:
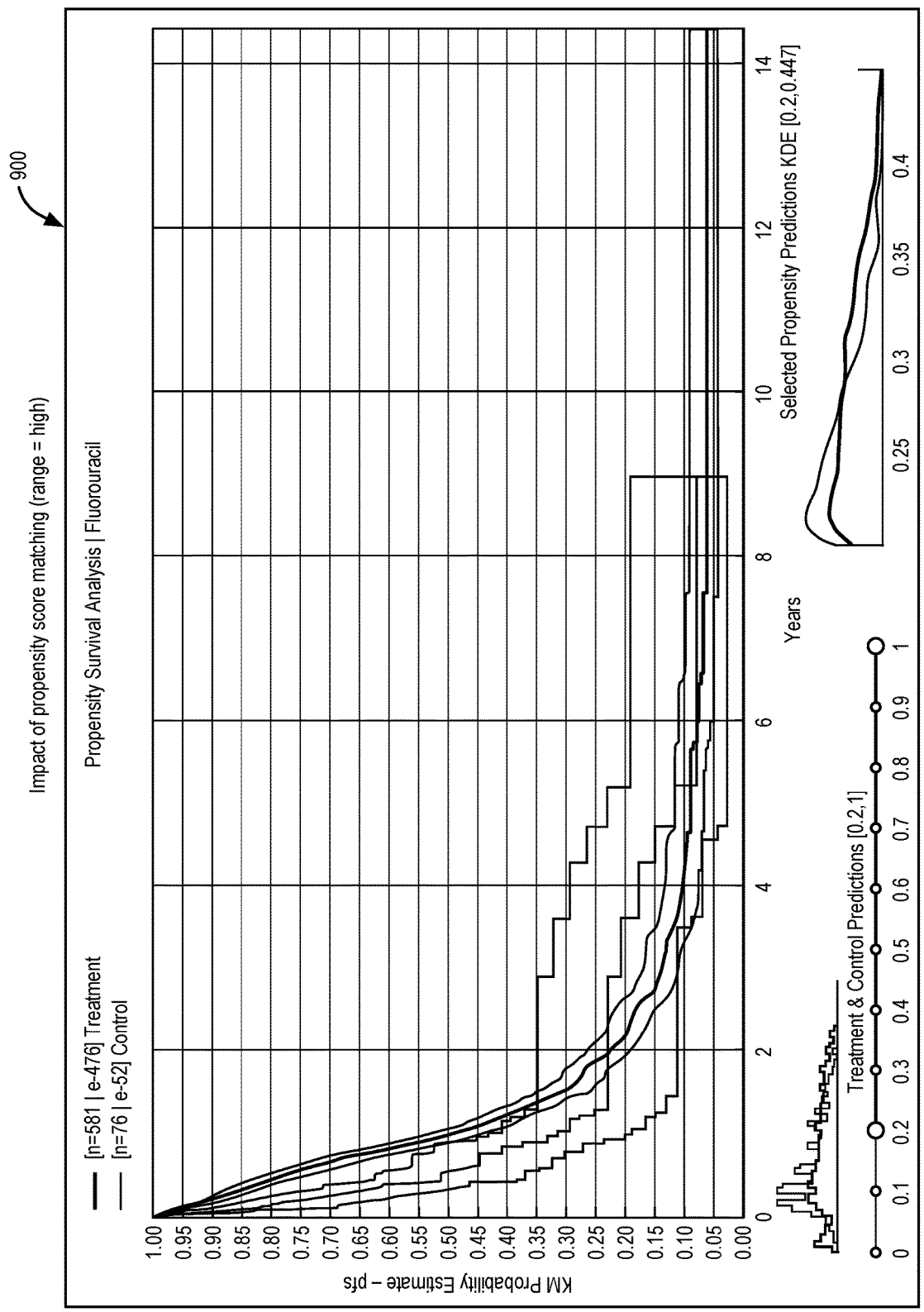
FIGS. 11A and 11B are diagrams collectively illustrating the user interface of FIGS. 9A and 9B where a high propensity value threshold is obtained, in accordance with some embodiments of the present disclosure.
Figure 11B:

FIGS. 9A and 9B illustrate an example of an embodiment a tool user interface 900, demonstrating impact of obtaining a low propensity value threshold, with a range of between 0 and 0.1. The portions of the user interface 900 shown separately in FIGS. 9A and 9B can be displayed simultaneously on the user interface 900. FIGS. 10A and 10B illustrate an example of the tool user interface 900, demonstrating impact of obtaining a higher, mid-range (referred to as "mid") propensity value threshold of a range of between 0.1 and 0.2, and FIGS. 11A and 11B illustrate an example of the tool user interface 900, demonstrating impact of obtaining a high propensity value threshold with a range of between 0.2 and 1. The user interface 900 can be similar to the user interface 600 (FIGS. 6A-6C) such that the same base population is used for the evaluation of effect of fluorouracil on colon cancer.

As shown in FIGS. 9A, 10A, and 11B, a selection of certain range for a propensity value threshold affects a number of subjects selected from the treatment and control groups, and consequently features characterizing the groups. Thus, increasing the range for a propensity value threshold generally results in increasing the size of the matched groups.

Figure 12:
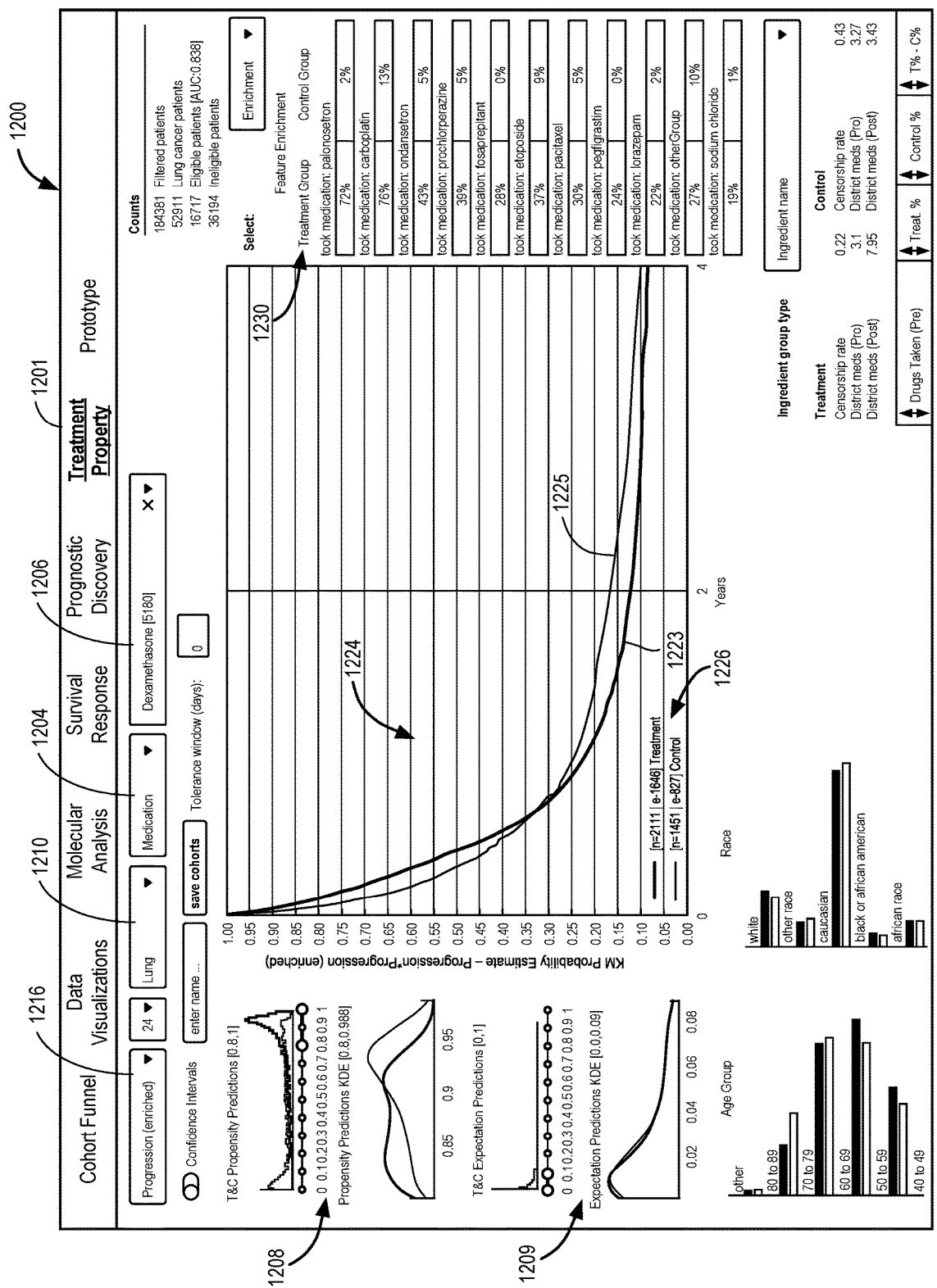
FIG. 12 illustrates an example of a user interface that includes both a user interface element configured to receive a propensity value threshold and a user interface element configured to receive a survival propensity value threshold, in accordance with some embodiments of the present disclosure.

As mentioned above, in some embodiments, in addition to being configured to receive a selection of a propensity value threshold related to a probability of a certain treatment being administered to a subject, a tool user interface can be configured to receive a selection of a survival propensity value threshold. FIG. 12 illustrates an example of a user interface 1200 that includes both a user interface element 1208 configured to receive a propensity value threshold, and a user interface element 1209 configured to receive a survival propensity value threshold. The user interface 1200 may be implemented, for example, as part of a system for predicting and analyzing patient cohort response, progression, and survival, as described, for example, in U.S. Provisional Patent Application No. 62/786,739 filed Dec. 31, 2018, which is incorporated by reference herein in its entirety.

In the example of FIG. 12, the user interface elements 1208 and 1209 are sliders configured to receive input regarding a range of values from 0 to 1, with a step of 0.1. As shown in FIG. 12, the user interface element 1208 is additionally associated with graphs displaying KDEs (kernel density estimators) for treatment and control ("T&C") propensity predictions, and the user interface element 1209 is additionally associated with graphs displaying KDEs for treatment and control ("T&C") expectation predictions.

As mentioned above, the techniques described in the present disclosure may be included or otherwise associated with any suitable tool that can make use of propensity scoring of subjects in a population. Thus, the tool user interface 1200 of FIG. 12 includes several menu tabs, and the "Treatment Propensity" tab 1201 is shown to be selected for the implementation of an analysis in accordance with some embodiments of the present disclosure.

In FIG. 12, a survival objective representation element 1216 shows a progression (enriched) selection, a user interface element 1210 shows a selection of a lung cancer, an event type user interface element 1204 shows a selection of a medication type of event, and an event user interface element 1206 shows a selection of a specific medication, dexamethasone. In this example, 2111 subjects from a base population of subjects being analyzed are included in a treatment cohort and 1451 subjects from the base population are included in a control cohort, as shown at a location 1226 of the user interface 1200. Propensity survival analytics includes survival curves 1224 (KM probability estimate, Progression*Progression (enriched) vs. years) comprising a survival curve 1223 for the treatment group (shown in blue color) and a survival curve 1225 for the control group (shown in grey color). Bar charts illustrating comparison between the treatment group (top bars) and control group (bottom bars) are shown for age group and race features on the bottom left of the user interface 1200.

In the illustrated example, the tool user interface 1200 includes a feature enrichment module 1230 showing comparison of enriched features for the treatment group and the control group. The feature enrichment module 1230 shows, for a specific medication, a percentage of subjects in the treatment group who took the medication and a respective percentage of subjects in the control group who could have been administered the medication.

It should be appreciated that a tool user interface implementing the techniques in accordance with embodiments of the present disclosure can include various user interface elements that can receive and/or display various information.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

Several aspects are described above with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

CONCLUSION

The methods described herein provide improved cancer classification for patients. With improved accuracy and higher resolution over previous methods, the predictive algorithms provided herein can be used to resolve the diagnoses of tumors of unknown origin. With such increased resolution in the classification outputs, additional patients will receive more accurate diagnoses and more informed treatments.

REFERENCES CITED

All references cited herein are incorporated herein by reference in their entirety and for all purposes to the same extent as if each individual publication or patent or patent application was specifically and individually indicated to be incorporated by reference in its entirety for all purposes.

What is claimed is:

1. A computer-implemented method of evaluating an effect of an event on a first condition using a base population of subjects that each have the first condition, the method comprising:
   (A) obtaining data for the base population that includes, for each respective subject in the base population, a respective plurality of features and a respective value for a survival objective;
   (B) obtaining a propensity value threshold;
   (C) identifying a first plurality of subjects in the base population and a start date of an event for each respective subject in the first plurality of subjects at which the respective subject incurs the event;
   (D) using a propensity scoring model to select a second plurality of subjects from the base population, wherein the propensity scoring model is a random forest model, a gradient boosting model, a neural network model, a boosted CART model, a generalized boosted model, or a greedy nearest neighbor model, wherein the propensity scoring model is generated and trained on the base population, based at least in part on a respective plurality of features, and wherein the second plurality of subjects are other than the first plurality of subjects, by performing a first procedure that comprises, for a respective subject in the base population:
      (i) applying a corresponding plurality of features for the respective subject in the base population to the propensity scoring model tuned to the propensity value threshold, wherein a first subset of the corresponding plurality of features for which data was acquired for the respective subject is associated with a respective time period and a second subset of the corresponding plurality of features for which data was acquired for the respective subject are static, thereby obtaining one or more anchor point predictions for the respective subject, wherein each anchor point prediction is associated with a corresponding instance of time in the respective time period and includes a probability that a corresponding instance of time is a start date for the event for the respective subject, and
      (ii) assigning an anchor point for the respective subject to be the corresponding instance of time that is associated with the anchor point prediction that has a greatest probability across the anchor point predictions; and
   (E) determining a first value for the survival objective of the first plurality of subjects and a second value for the survival objective of the second plurality of subjects using the event start date for each respective subject in the first plurality of subjects and the anchor point for each respective subject in the second plurality of subjects, in order to evaluate the effect of the event on the first condition.

2. The computer-implemented method of claim 1, wherein the obtaining (B), identifying (C), using (D) and determining (E) is performed in response to a corresponding instruction received via a user interface.

3. The computer-implemented method of claim 2, further comprising displaying a result of the determining (E) on the user interface.

4. The computer-implemented method of claim 1, wherein the propensity value threshold is obtained based on user input received via the user interface.

5. The computer-implemented method of claim 1, wherein the event comprises application of a medication to a subject.

6. The computer-implemented method of claim 1, wherein the event comprises a medical procedure performed on a subject.

7. The computer-implemented method of claim 6, wherein the medic al procedure is a surgical procedure or a radiation treatment.

8. The computer-implemented method of claim 1, wherein the propensity scoring model is a binary classification model.

9. The computer-implemented method of claim 8, wherein the binary classification algorithm is a random forest model.

10. The computer-implemented method of any one of claims 1-9, wherein the survival objective is time until death, time until progression of the first condition, or time until an adverse event associated with the first condition is incurred.

11. The computer-implemented method of claim 1, comprising using the propensity scoring model to identify the first plurality of subjects from the base population.

12. The computer-implemented method of claim 11, wherein the propensity scoring model assigns a propensity score to each subject in the first plurality of subjects and the propensity scoring model assigns a propensity score to each subject in the second plurality of subjects, and wherein a propensity score for a subject reflects a likelihood of the subject incurring the event conditional on a corresponding plurality of features of the subject.

13. The computer-implemented method of claim 12, wherein the method further comprises identifying the first plurality of subjects and the second plurality of subjects based on a propensity score assigned to each subject in the first plurality of subjects and in the second plurality of subjects, with the proviso that each subject in the first plurality of subjects and each subject in the second plurality of subjects is assigned a corresponding propensity score that matches the propensity value threshold.

14. The computer-implemented method of claim 1, wherein the plurality of features for the respective subject comprises a corresponding plurality of demographic features for the respective subject and a plurality of clinical temporal data for the respective subject.

15. The computer-implemented method of claim 14, wherein the plurality of features further comprises a corresponding plurality of genomic features for the respective subject.

16. The computer-implemented method of claim 11, wherein the method assigns each subject in the base population into one of the first plurality of subjects, the second plurality of subjects, or a group of non-matching subjects that are not assigned to the first plurality of subjects or the second plurality of subjects.

17. The computer-implemented method of claim 1, wherein the method further comprises receiving an indication of the first condition and the event based on user input received via a user interface.

18. The computer-implemented method of claim 1, wherein the first plurality of subjects and the second plurality of subjects are selected by the identifying (C) and using (D) such that the first plurality of subjects and the second plurality of subjects have the same number of subjects.

19. The computer-implemented method of claim 1, wherein the propensity value threshold comprises a propensity value range.

20. The method of claim 19, wherein the propensity value range is between 0 and 1.

21. The computer-implemented method of claim 1, wherein the first condition is breast cancer, colon cancer, lung cancer, ovary cancer, or prostate cancer.

22. The computer-implemented method of claim 1, wherein
the survival objective of the first plurality of subjects is determined through a first Kaplan-Meier estimate, and
the survival objective of the second plurality of subjects is determined through a second Kaplan-Meier estimate.

23. The computer-implemented method of claim 1, wherein the respective time period is a period of days, months or years.

24. The computer-implemented method of claim 1, wherein, for a respective subject in the second plurality of subjects:
the one or more anchor point predictions for the respective subject is a plurality of anchor point predictions,
a first feature in the first subset of the corresponding plurality of features is measured a plurality of times across the respective time period, and
each measurement instance of the first feature is used in a different propensity model calculation to derive a different anchor point prediction in the anchor point predictions.

25. The computer-implemented method of claim 1, wherein a feature in the second subset of features is gender, race, or year of birth, family history, body weight, size, or body mass index.

26. The computer-implemented method of claim 1, wherein a feature in the first subset of features is months since birth, smoking status, menopausal status, time since menopause, time since last smoked, primary cancer site observed, metastasis site observed, cancer recurrence site observed, tumor characterization, medical procedure performed, medication type administered, radiotherapy treatment administered, time since primary diagnosis, time since predefined cancer stage diagnosed, time since metastasis, time since last recurrence of cancer, time since medical procedure performed, time since predefined medication taken, time since radiotherapy treatment administered, imaging procedure performed, change in tumor characteristic, rate of change in tumor characteristic, or predetermined response observed.

27. The computer-implemented method of claim 1, wherein a first feature in the plurality of features is obtained from a biological sample of the respective subject and corresponds to a DNA for a predetermined human gene.

28. The computer-implemented method of claim 27, wherein the first feature is a count of germline mutations observed for the DNA in the biological sample of the respective subject.

29. The computer-implemented method of claim 27, wherein the first feature is a count of somatic mutations observed for the DNA in the biological sample of the respective subject.

30. The computer-implemented method of claim 1, wherein a first feature in the plurality of features is a number of somatic mutations on a predetermined chromosome as determined by sequencing DNA from a biological sample obtained from the respective subject.

31. The computer-implemented method of claim 1, wherein a first feature in the plurality of features is a number of germline mutations on a predetermined chromosome as determined by sequencing DNA from a biological sample obtained from the respective subject.

32. The computer-implemented method of claim 1, wherein a first feature in the plurality of features is a number of genes with mutations on a predetermined chromosome as determined by sequencing DNA from a biological sample obtained from the respective subject.

33. The computer-implemented method of claim 1, wherein a first feature in the plurality of features is a mutation density of a predetermined chromosome as determined by sequencing DNA from a biological sample obtained from the respective subject.

34. The computer-implemented method of claim 1, wherein a first feature in the plurality of features is a number of mutations of a defined mutational class of a predetermined chromosome as determined by sequencing DNA from a biological sample obtained from the respective subject.

35. The computer-implemented method of claim 34, wherein the defined mutational class is single nucleotide polymorphism (SNP), multiple nucleotide polymorphism (MNP), insertions (INS), deletion (DEL), or translocation.

36. A computer system having one or more processors, and memory storing one or more programs for execution by the one or more processors, the one or more programs comprising instructions for performing a method of evaluating an effect of an event on a first condition using a base population of subjects that each have the first condition, the method comprising:
(A) obtaining data for the base population that includes, for each respective subject in the base population, a respective plurality of features and a respective value for a survival objective;
(B) obtaining a propensity value threshold;
(C) identifying a first plurality of subjects in the base population and a start date of an event for each respective subject in the first plurality of subjects at which the respective subject incurs the event;

(D) using a propensity scoring model to select a second plurality of subjects from the base population, wherein the propensity scoring model is a random forest model, a gradient boosting model, a neural network model, a boosted CART model, a generalized boosted model, or a greedy nearest neighbor model, wherein the propensity scoring model is generated and trained on the base population, based at least in part on a respective plurality of features, and wherein the second plurality of subjects are other than the first plurality of subjects, by performing a first procedure that comprises, for a respective subject in the base population:

(i) applying a corresponding plurality of features for the respective subject in the base population to the propensity scoring model tuned to the propensity value threshold, wherein a first subset of the corresponding plurality of features for which data was acquired for the respective subject is associated with a respective time period and a second subset of the corresponding plurality of features for which data was acquired for the respective subject are static, thereby obtaining one or more anchor point predictions for the respective subject, wherein each anchor point prediction is associated with a corresponding instance of time in the respective time period and includes a probability that a corresponding instance of time is a start date for the event for the respective subject, and (ii) assigning an anchor point for the respective subject to be the corresponding instance of time that is associated with the anchor point prediction that has a greatest probability across the anchor point predictions; and (E) determining a first value for the survival objective of the first plurality of subjects and a second value for the survival objective of the second plurality of subjects using the event start date for each respective subject in the first plurality of subjects and the anchor point for each respective subject in the second plurality of subjects, in order to evaluate the effect of the event on the first condition.

37. The computer system of claim 36, wherein the obtaining (B), identifying (C), using (D) and determining (E) is performed in response to a corresponding instruction received via a user interface.

38. The computer system of claim 36, wherein the survival objective is time until death, time until progression of the first condition, or time until an adverse event associated with the first condition is incurred.

39. The computer system of claim 36, further comprising using the propensity scoring model to identify the first plurality of subjects from the base population, wherein the propensity scoring model assigns a propensity score to each subject in the first plurality of subjects and the propensity scoring model assigns a propensity score to each subject in the second plurality of subjects, and a propensity score for a subject reflects a likelihood of the subject incurring the event conditional on a corresponding plurality of features of the subject.

40. The computer system of claim 36, wherein, for a respective subject in the second plurality of subjects:

the one or more anchor point predictions for the respective subject is a plurality of anchor point predictions, a first feature in the first subset of the corresponding plurality of features is measured a plurality of times across the respective time period, and each measurement instance of the first feature is used in a different propensity model calculation to derive a different anchor point prediction in the plurality of anchor point predictions.

41. A non-transitory computer readable storage medium, wherein the non-transitory computer readable storage medium stores instructions, which when executed by a computer system, cause the computer system to perform a method of evaluating an effect of an event on a first condition using a base population of subjects that each have the first condition, the method comprising:

(A) obtaining data for the base population that includes, for each respective subject in the base population, a respective plurality of features and a respective value for a survival objective;

(B) obtaining a propensity value threshold;

(C) identifying a first plurality of subjects in the base population and a start date of an event for each respective subject in the first plurality of subjects at which the respective subject incurs the event;

(D) using a propensity scoring model to select a second plurality of subjects from the base population, wherein the propensity scoring model is a random forest model, a gradient boosting model, a neural network model, a boosted CART model, a generalized boosted model, or a greedy nearest neighbor model, wherein the propensity scoring model is generated and trained on the base population, based at least in part on a respective plurality of features, and wherein the second plurality of subjects are other than the first plurality of subjects, by performing a first procedure that comprises, for a respective subject in the base population:

(i) applying a corresponding plurality of features for the respective subject in the base population to the propensity scoring model tuned to the propensity value threshold, wherein a first subset of the corresponding plurality of features for which data was acquired for the respective subject is associated with a respective time period and a second subset of the corresponding plurality of features for which data was acquired for the respective subject are static, thereby obtaining one or more anchor point predictions for the respective subject, wherein each anchor point prediction is associated with a corresponding instance of time in the respective time period and includes a probability that a corresponding instance of time is a start date for the event for the respective subject, and (ii) assigning an anchor point for the respective subject to be the corresponding instance of time that is associated with the anchor point prediction that has a greatest probability across the anchor point predictions; and (E) determining a first value for the survival objective of the first plurality of subjects and a second value for the survival objective of the second plurality of subjects using the event start date for each respective subject in the first plurality of subjects and the anchor point for each respective subject in the second plurality of subjects, in order to evaluate the effect of the event on the first condition.

42. The non-transitory computer readable storage medium of claim 41, wherein the obtaining (B), identifying (C), using (D) and determining (E) is performed in response to a corresponding instruction received via a user interface.

43. The non-transitory computer readable storage medium of claim 41, wherein the survival objective is time until death, time until progression of the first condition, or time until an adverse event associated with the first condition is incurred.

44. The non-transitory computer readable storage medium of claim 41, wherein the method of evaluating an effect of an event on a first condition using a base population of subjects that each have the first condition further comprises using the propensity scoring model to identify the first plurality of subjects from the base population, wherein the propensity scoring model assigns a propensity score to each subject in the first plurality of subjects and the propensity scoring model assigns a propensity score to each subject in the second plurality of subjects, and a propensity score for a subject reflects a likelihood of the subject incurring the event conditional on a corresponding plurality of features of the subject.

45. The non-transitory computer readable storage medium of claim 41, wherein, for a respective subject in the second plurality of subjects:
  the one or more anchor point predictions for the respective subject is a plurality of anchor point predictions,
  a first feature in the first subset of the corresponding plurality of features is measured a plurality of times across the respective time period, and
  each measurement instance of the first feature is used in a different propensity model calculation to derive a different anchor point prediction in the plurality of anchor point predictions.

* * * * *